(12) United States Patent
Brewer et al.

(10) Patent No.: US 9,764,109 B2
(45) Date of Patent: Sep. 19, 2017

(54) METHOD OF CORRELATING BRAIN ACTIVITY

(71) Applicant: Yale University, New Haven, CT (US)

(72) Inventors: Judson Brewer, New Haven, CT (US); Dustin Scheinost, New Haven, CT (US)

(73) Assignee: Yale University, New Haven, CT (US)

( * ) Notice: Subject to any disclaimer, the term of this patent is extended or adjusted under 35 U.S.C. 154(b) by 82 days.

(21) Appl. No.: 13/680,744

(22) Filed: Nov. 19, 2012

(65) Prior Publication Data

US 2013/0131438 A1 May 23, 2013

Related U.S. Application Data

(60) Provisional application No. 61/561,871, filed on Nov. 19, 2011.

(51) Int. Cl.
*A61M 21/02* (2006.01)
*A61B 5/055* (2006.01)
*A61B 5/0476* (2006.01)
*A61B 5/00* (2006.01)

(52) U.S. Cl.
CPC .......... *A61M 21/02* (2013.01); *A61B 5/0476* (2013.01); *A61B 5/055* (2013.01); *A61B 5/486* (2013.01); *A61B 5/4064* (2013.01)

(58) Field of Classification Search
CPC ....... A61B 5/055; A61B 5/486; A61B 5/0042; A61B 5/04; A61B 5/742; A61B 6/501; G09B 19/00

USPC ..................... 600/26, 28, 544, 545
See application file for complete search history.

(56) References Cited

U.S. PATENT DOCUMENTS 4,949,726 A * 8/1990 Hartzell ............. A61B 5/04845
273/460
2009/0069707 A1* 3/2009 Sandford ...................... 600/545

OTHER PUBLICATIONS

Christoff K, Gordon AM, Smallwood J, Smith R, Schooler JW. Experience Samping During fMRI Reveals Default Network and Executive System Contributions to Mind Wandering. May 26, 2009. PNAS 106: 21: pp. 8719-8724.*

(Continued)

*Primary Examiner* — Christine H Matthews
*Assistant Examiner* — Joshua D Lannu
(74) *Attorney, Agent, or Firm* — Saul Ewing LLP; Kathryn Doyle

(57) ABSTRACT

The present invention includes systems and methods of using real-time neurofeedback to improve the correspondence between first-person experience and specific brain activation patterns in a manner that minimally affects the experience itself. The present invention provides meditators the ability to enhance their control over their own brain activity, such as posterior cingulate cortex (PCC) activation. The present invention also provides methods for treating a disease or disorder of a subject by measuring the subject's brain activity via fMRI, presenting a representation of the measured brain activity to the subject, and instructing the subject to reduce the represented brain activity by altering their meditative state. The present invention also provides a system and method of using fMRI neurofeedback to directly correlate subjective experience with neural activation.

11 Claims, 7 Drawing Sheets

(56) References Cited

OTHER PUBLICATIONS

"Physiological self-regulation of regional brain activity suing real-time functional magnetic imaging (fMRI): methodology and exemplary data". Nikolaus Weiskopf, Ralf Veit, Michael Erb, Klaus Mathiak, Wolfgang Grodd, Rainer Goebel, and Niels Birbaumer. Neuroimage 19 (2003) 577-586.*
Nikolaus Weiskopf, Ralf Veit, Michael Erb, Klaus Mathiak, Wolfgang Grodd, Rainer Goebel, Niels Birbaumer. Physiological self-regulation of regional brain activity using real-time functional magnetic resonance imaging (fMRI): methodology and exemplary data. Neuroimage. vol. 19, Issue 3, Jul. 2003, pp. 577-586.*
Andrews-Hanna et al., "Functional-Anatomic Fractionation of the Brain's Default Network", Neuron. 65(4):550-562 (2010).
Birbaumer et al., "Brain-computer interface in paralysis," 21 (6) *Current Opinion in Neurology* 634-38 (2008).
Bishop et al., "Mindfulness: A Proposed Operational Definition", Clinical Psychology: Science and Practice, 11(3):230-241 (2004).
Bowen et al., "Mindfulness-Based Relapse Prevention for Substance Abuse Disorders: A Pilot Efficacy Trial", Subst. Abus. 30(4):295-305 (2009).
Brefczynski-Lewis et al., "Neural correlates of attentional expertise in long-term meditation practitioners", PNAS, 104(27):11483-11488 (2007).
Brewer et al., "Mindfulness Training and Stress Reactivity in Substance Abuse: Results from a Randomized, Controlled Stage I Pilot Study", Subst. Abus. 30(4):306-317 (2009).
Brewer et al., "Meditation experience is associated with differences in default mode network activity and connectivity," 108(50) *PNAS* 20254-9 (2011).
Buckner et al., "The Brain's Default Network: Anatomy, Function, and Relevance to Disease," 1124 *Annals of the New York Academy of Science* 1-38 (2008).
Caria et al., "Regulation of anterior insular cortex activity using real-time fMRI", Neuroimage, 35:1238-1246 (2007).
Caria et al, "Volitional Control of Anterior Insula Activity Modulates the Response to Aversive Stimuli. A Real-Time Functional Magnetic Resonance Imaging Study," 68(5) *Biological Psychiatry* 425-32 (2010).
Castellanos et al., "Cingulate—Precuneus Interactions: A New Locus of Dysfunction in Adult Attention-Deficit/Hyperactivity Disorder," 63(3) *Biol. Psychiatry* 332-37 (2008).
Chalmers, "What is a neural correlate of consciousness?" in *Neural Correlates of Consciousness: Empirical and Conceptual Questions* 17-40 (T. Metzinger ed. 2000).
Chiesa, "Vipassana meditation: systematic review of current evidence," 16(1) *J. Altern. Complement. Med*, 37-46 (2010).
Christoff et al., "Experience sampling during fMRI reveals default network and executive system contributions to mind wandering", PNAS, 106(21):8719-8724 (2009).
Decharms et al., "Learned regulation of spatially localized brain activation using realtime fMRI," 21(1) *Neuroimage* 436-43 (2004).
Decharms et al., "Control over brain activation and pain learned by using real-time functional MRI", PNAS, 102(51):18626-18631 (2005).
Farb et al., "Attending to the present: mindfulness meditation reveals distinct neural modes of self-reference," Soc. Cogn. Affect. Neurosci., 2:313-322 (2007).
Farb et al., "Minding One's Emotions: Mindfulness Training Alters the Neural Expression of Sadness", Emotion, 10(1):25-33 (2010).
Goldin et al., "Mindfulness meditation training and self-referential processing in social anxiety disorder: Behavioral and neural effects," 23(3) *J. Cognitive Psychotherapy* 24257 (2009).
Goldin et al., "Effects of Mindfulness-Based Stress Reduction (MBSR) on Emotion Regulation in Social Anxiety Disorder", Emotion, 10(1):83-91 (2010).
Gunaratana, *Mindfulness in Plain English*, Boston: Wisdom Publications (2002).

Hamilton et al., "Modulation of Subgenual Anterior Cingulate Cortex Activity With Real-Time Neurofeedback," 32(1) *Human Brain Mapping* 22-31 (2011).
Hasenkamp et al., "Mind wandering and attention during focused meditation: A fine-grained temporal analysis of fluctuating cognitive states", Neuroimage, 1-11 (2011).
Holzel et al., "Differential engagement of anterior cingulate and adjacent medial frontal cortex in adept mediators and non-mediators," Neurosci. Lett., 421:16-21 (2007).
Holzel et al., "Mindfulness practice leads to increases in regional brain gray matter density", Psychiatry Res., 191(1):36-43 (2011).
Ives-Deliperi et al., "The neural substrates of mindfulness: An fMRI investigation", Social Neuroscience, 6(3):231-242 (2011).
Jha et al., "Mindfulness training modifies subsystems of attention", Cognitive, Affective & Behavioral Neuroscience, 7(2):109-119 (2007).
Kabat-Zinn et al., "The clinical use of mindfulness mediation for the self-regulation of chronic pain," 8(2) *J. Behav. Med*. 163-90 (1985).
Kelley, et al., "Finding the self? An event-related fMRI study," 14(5) *J. Cogn. Neurosci*, 785-94 (2002).
Killingsworth et al., "A Wandering Mind Is an Unhappy Mind", Science, 330:932-939 (2010).
Kilpatrick et al., "Impact of Mindfulness-Based Stress Reduction Training on Intrinsic Brain Connectivity", Neuroimage, 56(1):290-298 (2011).
Kingston et al., "A pilot randomized control trial investigating the effect of mindfulness practice on pain tolerance, psychological well-being, and physiological activity", Journal of Psychosomatic Research, 62:279-300 (2007).
Langleben et al., "Telling Truth From Lie in Individual Subjects With fast Event-Related fMRI", Human Brain Mapping, 26:262-272 (2005).
Luders et al., "Enhanced Brain Connectivity in Long-term Meditation Practitioners", Neuroimage, 57(4):1308-1316 (2011).
Luders et al., "The underlying anatomical correlates of long-term meditation: Larger hippocampal and frontal volumes of gray matter", Neuroimage, 45(3):672-678 (2009).
Lutz et al., "Attention regulation and monitoring in meditation", Trends Cogn. Sci., 12(4):163-169 (2008).
Lutz et al., "Mental Training Enhances Attentional Stability: Neural and Behavioral Evidence", The Journal of Neuroscience, 29(42):13418-13427 (2009).
Lutz et al., "Neurophenomenology", Journal of Consciousness Studies, 10(9-10):31-52 (2003).
Manna et al., "Neural correlates of focused attention and cognitive monitoring in meditation," 82(1-2) *Brain Res. Bull*. 46-56 (2010).
Mason et al., "Wandering Minds: The Default Network and Stimulus-Independent Thought", Science, 315:393-396 (2007).
Monti et al., "Willful Modulation of Brain Activity in Disorders of Consciousness," N. Engl. J. Med., 362(7):579-589 (2010).
Moore & Malinowski, "Meditation, mindfulness and cognitive flexibility," *Conscious Cogn*. 176-86 (2009).
Nisbett et al., "Telling more than we can know: verbal reports on mental processes," Psychological Review, 84(3):231(1977).
Northoff et al., "Self-referential processing in our brain—A meta-analysis of imaging studies on the self", Neuroimage, 31:440-457 (2006).
Owen and Coleman, "Functional neuroimaging of the vegetative state," 9(3) *Nat. Rev. Neurosci*. 235-43 (2008).
Poldrack, "Can cognitive processes be inferred from neuroimaging data?" 10(2) *Trends in Cognitive Sciences* 59-63 (2006).
Raichle et al., "A default mode of brain function", PNAS, 98(2):676-682 (2001).
Simpson et al., "Emotion-induced changes in human medial prefrontal cortex: II. During anticipatory anxiety", PNAS, 98(2):688-693 (2001).
Spence et al., "A cognitive neurobiological account of deception: evidence from functional neuroimaging", Phil. Trans. R. Soc. Lond. B, 359:1755-1762 (2004).
Tang et al., "Short-term meditation induces white matter changes in the anterior cingulate", PNAS, 107(35):15649-15652 (2010).

(56) References Cited

OTHER PUBLICATIONS

Taylor, et al., "Impact of mindfulness on the neural responses to emotional pictures in experienced and beginner meditators," 57(4) *Neuroimage* 1524-33.

Teasdale et al., "Prevention of Relapse/Recurrence in Major Depression by Mindfulness-Based Cognitive Therapy," 68(4) *J. Consult. Clin. Psychol.* 615-23 (2010).

Weissman et al., "The neural bases of momentary lapses in attention," 9(7) *Nat. Neurosci.* 971-78 (2006).

* cited by examiner

METHOD OF CORRELATING BRAIN ACTIVITY

CROSS REFERENCE TO RELATED APPLICATIONS

This application is entitled to priority under 35 U.S.C. §119(e) to U.S. Provisional Patent Application No. 61/561,871, filed on Nov. 19, 2011, which is hereby incorporated herein by reference in its entirety.

STATEMENT REGARDING FEDERALLY SPONSORED RESEARCH OR DEVELOPMENT

This invention was made with government support under DA000167 and DA029163 awarded by National Institute of Health. The government has certain rights in the invention.

BACKGROUND OF THE INVENTION

Mind-wandering is not only a common activity, present in roughly 50% of our awake life, but is also associated with lower levels of happiness (Killingsworth & Gilbert, 2010, Science 330(6006):932). Moreover, mind-wandering is known to correlate with neural activity in a network of brain areas that support self-referential processing, known as the Default Mode Network (DMN) (Mason et al., 2007, Science 315(5810):393; Raichle et al., 2001, Proc. Natl. Acad. Sci. USA 98(2):676; Christoff et al., 2009, Proc. Natl. Acad. Sci. USA 106(21):8719-8724; Simpson et al., 2001, Proc. Natl. Acad. Sci. USA. 98(2):688-693; Buckner R L, Andrews-Hanna J R, & Schacter D L (2008) The brain's default network: Anatomy, function, and relevance to disease, The year in cognitive neuroscience 2008, eds Kingstone A & Miller M B (Blackwell Publishing, Malden, Mass.), pp 1-38; Andrews-Hanna et al., 2010, Neuron 65(4):550-562). This network has been associated with processes ranging from attentional lapses to anxiety, as well as to clinical disorders such as Attention Deficit Hyperactivity Disorder (ADHD) and Alzheimer's Disease (Buckner R L, Andrews-Hanna J R, & Schacter D L (2008) The brain's default network: Anatomy, function, and relevance to disease, The year in cognitive neuroscience 2008, eds Kingstone A & Miller M B (Blackwell Publishing, Malden, Mass.), pp 1-38; Weissman et al., 2006, Nat. Neurosci. 9(7):971-978; Castellanos et al., 2008, Biol. Psychiatry 63(3):332-337).

One potential way to reduce DMN activity is through the practice of mindfulness-based meditation. Mindfulness, a core element of diverse forms of meditation, is thought to include two complementary components: 1) maintaining attention on the immediate experience, and 2) maintaining an attitude of acceptance toward this experience (Bishop et al., 2004, Clin. Psychol 11(3):230-241). Specific types of mindfulness meditation have been taught in a standardized fashion for decades as a mainstay of mindfulness training in community and clinical settings (e.g., through traditional teacher- or retreat-led mindfulness meditation practice, Mindfulness Based Stress Reduction, Mindfulness Based Cognitive Therapy and Mindfulness Based Relapse Prevention) (Gunaratana H (2002), Mindfulness in Plain English (Wisdom Publications, Somerville, Mass.); Chiesa, 2010, J. Altern. Complement. Med. 16(1):37-46; Kabat-Zinn et al., 1985, J Behav. Med. 8(2):163-190; Teasdale et al., 2010, J. Consult. Clin. Psychol. 68(4):615-623; Bowen et al., 2009, Substance Abuse 30(4):295-305).

Three standard and commonly used meditation practices are: Concentration, Loving-kindness, and Choiceless Awareness. Through focused attention on a single object of awareness (typically the breath), Concentration meditation is intended to help individuals retrain their minds from habitually engaging in self-related pre-occupations (such as thinking about the past or future, or reacting to stressful stimuli) to more present moment awareness (Gunaratana H (2002), Mindfulness in Plain English (Wisdom Publications, Somerville, Mass.)). Loving-kindness meditation is hypothesized to foster acceptance, both of oneself and others, as well as to increase concentration. It is practiced through directed well-wishing, typically by repetition of phrases such as "may [I/someone else] be happy" (Gunaratana H (2002), Mindfulness in Plain English (Wisdom Publications, Somerville, Mass.)). Choiceless Awareness is hypothesized to broaden the scope of mindfulness to all aspects of experience, whether during formal meditation practice or everyday life, via directly attending to whatever arises in one's conscious field of awareness at any moment (Gunaratana H (2002), Mindfulness in Plain English (Wisdom Publications, Somerville, Mass.); Lutz et al., 2008, Trends in Cognitive Sciences 12(4):163-169). During such training, meditators learn to clearly identify when self-related thoughts, emotions and body sensations are occurring, and to differentiate identification of these from identifying with them (e.g. awareness that anger is present vs. "I am angry"). That is, meditators practice noticing when they are identifying with an object, and when this occurs, to "let go" and bring their attention back to the present moment. Across these practices, one common aim is to reverse the habit of mind-wandering, which has been defined as "thinking about something other than what [one is] currently doing" (Killingsworth & Gilbert, 2010, Science 330(6006):932). In other words, the meditator's task is to remain aware from moment to moment, and self-identification is included in the off-task category of mind-wandering. Importantly, this information processing task, common to all three of these meditation techniques, is a training of attention away from self-reference and mind-wandering—and potentially away from default-mode processing.

Clinically, mindfulness training has shown benefit for the treatment of pain (Kabat-Zinn et al., 1985, J Behav. Med. 8(2):163-190), substance use disorders (Bowen et al., 2009, Substance Abuse 30(4):295-305; Brewer et al., 2009, Substance Abuse 30(4):306-317), anxiety disorders (Goldin et al., 2009, J. Cognitive Psychotherapy 23(3):242-257), and depression (Teasdale et al., 2010, J. Consult. Clin. Psychol. 68(4):615-623), while also helping to increase psychological well-being in non-clinical populations (Kingston et al., 2007, J Psychosom. Res. 62(3):297-300). These outcomes have been associated with changes in basic psychological processes such as improved attentional focus (Jha et al., 2007, Cogn Affect Behav Neurosci 7(2):109-119; Lutz et al., 2009, J Neurosci 29(42):13418-13427), improved cognitive flexibility (Moore & Malinowski, 2009, Conscious Cogn 18(1):176-186), reduced affective reactivity (Farb et al., 2010, Emotion 10(1):25-33; Goldin & Gross, 2010, Emotion 10(1):83-91), and modification or shifts away from distorted or exaggerated view of oneself (Goldin et al., 2009, J. Cognitive Psychotherapy 23(3):242-257; Farb et al., 2007, Soc Cogn Affect Neurosci 2(4):313-322). However, direct links between the meditative practices that are part of mindfulness training and changes in neurobiology remain elusive. Investigation of the brain activation patterns during specific meditation practices may help to identify potential neural mechanisms of mindfulness training.

Previous studies have examined individuals using meditation techniques from different traditions (e.g. Tibetan Buddhism, Zen Buddhism, Vipassana, Mindfulness-Based Stress Reduction, etc.), and employed a wide variety of experimental methods ranging from performance of different types of meditation, to introduction of emotionally-charged sounds during meditation, to assessment of functional connectivity (Lutz et al., 2008, Trends in Cognitive Sciences 12(4):163-169; Manna et al., 2010, Brain Res Bull 82(1-2):46-56; Ives-Deliperi et al., 2011, Soc Neurosci. 6(3):231-42; Brefczynski-Lewis et al., 2007, Proc Natl Acad Sci USA 104(27):11483-11488; Holzel et al., 2007, Neurosci. Lett. 421(1):16-21). However, given the methodological differences and in some cases, difficulty in finding appropriately-matched controls, no consensus has emerged as to what the neural mechanisms of meditation are, or how they may underlie the behavioral changes that have been observed after mindfulness training.

Finding the connection between the mind and the brain has fascinated neuroscientists for centuries. A rich and complex history has emerged around the study of first-person subjective reporting in pursuit of understanding human experience. Recent technological advances have increasingly refined the objective measurement of neuronal processes that are present during human experience. However, links between these third-person measurements and first-person subjective reports have not been established due, at least in part, to several methodological challenges that are inherent in these methodologies. One of the main challenges in gathering subjective data is that self-reports can be inaccurate or biased (Nisbett & Wilson, 1977, Psychological Review 84(3):231). Another difficulty is in capturing and characterizing subjective experiences that may regularly reside outside of the conscious attention, such as the visual experience of seeing a color, or the auditory experience of listening to music. Additionally, people vary greatly in their ability to observe and report upon their experiences due to variability in the degree of their awareness of the contents of their own thoughts (Christoff, et al., 2009, Proc Natl Acad Sci USA 106(21):8719-8724) as well as fluctuations in their attention levels (Tononi & Koch, 2008, Ann N Y Acad Sci 1124(1):239-261). Furthermore, the act of generating a contemporaneous introspective report about an experience may serve to modify the experience itself (Lutz & Thompson, 2003, J. Consciousness Studies, 10(9-10): 31-52). For example, during introspective states such as meditation, the act of self-reflection pulls the individual out of the meditative state.

Relating subjective experiences and observed measurements or data seems simple enough in theory—gather a subjective first-person report about an experience as contemporaneously with the experience as possible, and gather third-person, objective data about behavior and brain processes simultaneously with the experience, then formulate concepts of principles of mechanisms that might underlie the experience based upon possible correlations between the two (Chalmers D J (2000), What is a neural correlate of consciousness? In: Neural Correlates of Consciousness: Empirical and Conceptual Questions, Metzinger T, ed., pp. 17-40. MIT Press: Cambridge, Mass.). This study design has proven to be more difficult in practice than it is in theory, as noted above. A number of recent studies have devised strategies for solving this problem. For example, in their investigation of the neural basis of mind-wandering, Christoff and colleagues used experience sampling during fMRI scanning, where, during a sustained attention task, subjects were intermittently asked to report where their attention was focused and whether they were on- or off-task preceding the query (Christoff, et al., 2009, Proc Natl Acad Sci USA 106(21):8719-8724). In this study, when subjects reported being off-task, they showed activation in the brain's default mode network (DMN), a network that reliably demonstrates involvement in both mind-wandering, and self-referential processing (Kelley, et al., 2002, J Cogn Neurosci 14(5):785-794; Northoff, et al., 2006, NeuroImage 31(1):440-457; Weissman, et al., 2006, Nat Neurosci 9(7):971-978; Mason, et al., 2007, Science 315(5810):393). Importantly, DMN activation was strongest when subjects were unaware of their own mind-wandering. Similarly, Hasenkamp and colleagues designed a method in which subjective information was simultaneously collected alongside fMRI data (Hasenkamp, et al., 2012, Neuroimage 59(1):750-60). They instructed meditators to meditate in the fMRI scanner and to press a button whenever they realized their minds had wandered. They differentially analyzed periods before and after the button press to determine brain activation patterns that were activated during presumptively different cognitive states. They, too, found that DMN activation correlated with mind-wandering, and that salience/attention network regions (e.g., dorsal anterior cingulate) were activated during awareness of mind-wandering. The objectivity of these studies is much improved over the use of retrospective recall alone. Nevertheless, a query or button press pulls individuals out of their current mind-state and the amount of subjective information that can be gathered during these types of experiments is somewhat limited, potentially leading to reverse inference of the cognitive processes that may actually be active at the times of the probes (Poldrack, 2006, Trends in Cognitive Sciences 10(2):59-63; Christoff, et al., 2009, Proc Natl Acad Sci USA 106(21):8719-8724). Thus, methods are still needed to refine the improved resolution afforded by using fMRI and self-report together, and to include more detailed subjective accounts in a less disruptive manner.

Another recent advance in the field of neuroimaging has been the development of real-time functional magnetic resonance imaging (rt-fMRI) neurofeedback. This technique retains the advantage of collecting objective sampling data contemporaneously with the event, as in the studies highlighted above, but has the theoretical advantage of reduced interference with the ongoing task or mind-state. Rt-fMRI neurofeedback has demonstrated preliminary success in several areas, including training the brain to manipulate external computerized devices such as prostheses (deCharms, et al., 2004, Neuroimage 21(1):436-443; Birbaumer, et al., 2008, Current Opinion in Neurology 21(6):634-638), communicating with locked-in patients or those previously thought to be in vegetative states (Owen and Coleman, 2008, Nat Rev Neurosci 9(3):235-243; Monti, et al., 2010, N Engl J Med 362(7):579-589), lie detection (Spence, et al., 2004, Philos Trans R Soc Lond B Biol Sci 359(1451):1755-62; Langleben, et al., 2005, Human Brain Mapping 26(4):262-272), controlling symptoms of chronic pain (deCharms, et al., 2005, Proc Natl Acad Sci USA 102(51):18626-18631) and modulating brain activation in regions associated with particular cognitive states (Caria, et al., 2007, Neuroimage 35(3): 1238-1246; Caria et al, 2010, Biological Psychiatry 68(5):425-432; Hamilton et al., 2011, Human Brain Mapping 32(1):22-31). However, it has not been used as a tool for exploring the correlates between 1st person subjective experience and brain activity. Such a modality would be especially useful in investigating neural correlates of introspective states that are conceptually difficult to convey in the first-person. For example, during the practice of mindfulness meditation, individuals practice dropping into states of "bare awareness," that, by definition, are free of all concepts including the concept of 'someone' paying attention (Gunaratana, H. (2002), Mindfulness in Plain English. Somerville, Mass., Wisdom Publications; Lutz, et al., 2008, Trends in Cognitive Sciences 12(4):163-169). Meditators can report being mindfully aware just after, but not during, moments of mindfulness because the act of observing disrupts the state itself. In extreme examples, such as absorptive concentration meditative states, awareness is described as "one-pointed" in the sense that conscious experience is so focused that it becomes literally a single point of focus (Buddhaghosa, A. (1991), The path of purification: Visuddhimagga, Buddhist Publication Society).

Therefore, there is a need in the art for rt-fMRI neurofeedback systems and methods to bridge the gap between subjective self-report, as individuals link their experience (including quality, such as depth) with neural activation in a time-precise manner, but with minimal interruption of their state from an external probe or other interference. The present invention satisfies this need.

SUMMARY OF THE INVENTION

The present invention relates to methods for enhancing a meditative state of a subject or treating a disease or disorder of a subject by measuring the subject's brain activity, presenting a representation of the measured brain activity to the subject, and instructing the subject to reduce the represented brain activity by altering their meditative state. The methods of the present invention can be used to reduce mind-wandering and stress. The methods of the present invention can also be used to treat Alzheimer's disease, Attention Deficit Hyperactivity Disorder (ADHD), depression, substance use disorders, disorders related to stress, and disorders related to mind-wandering.

In one embodiment, the method of the present invention is a method of enhancing a meditative state of a subject, comprising measuring a subject's brain activity; presenting a representation of the subject's brain activity to the subject simultaneously with the measuring of the subject's brain activity; and instructing the subject to alter their meditative state, such that the alteration to their meditative state decreases PCC activity. In another embodiment, the method of the present invention is a method of treating a disease or disorder of a subject, comprising measuring a subject's brain activity; presenting a representation of the subject's brain activity to the subject simultaneously with the measuring of the subject's brain activity; instructing the subject to enter into a meditative state; and instructing the subject to reduce the represented brain activity by enhancing their present meditative state.

The present invention also relates to methods correlating a subject's subjective report, or other information about the subject, to at least one neuronal process of the subject. In one embodiment, the method of the present invention is a method of correlating a subject's subjective report to at least one neuronal process of the subject, comprising measuring a subject's brain activity; presenting a representation of the subject's brain activity to the subject simultaneously with the measuring of the subject's brain activity; and instructing the subject to provide a report of their mental state while viewing the presented representation of the subject's brain activity. In another embodiment, the method of the present invention is a method of correlating information of a subject with a neuronal process of the subject, comprising detecting levels of brain activity of a subject from at least one brain region of the subject, and correlating the detected level of brain activity with information about the subject, such as the subject's physiological stress level, the subject's degree of self-referential activation, the subject's depth of meditation, and the subject's depth of "flow" state.

The measured or detected brain activity associated with the methods of the present invention can comprise activity in human brain regions such as the posterior cingulate cortex, dorsal anterior cingulate, dorsolateral prefrontal cortex, posterior parietal cortex, posterior insula, and thalamus. The measurement of the subject's brain activity of the present invention can be performed using functional Magnetic Resonance Imaging (fMRI) or electroencephalography (EEG). The representation of the measured brain activity of the present invention can be presented via a visual display, an interactive visual display, an auditory signal, or a tactile signal.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

DETAILED DESCRIPTION

Figure 1:
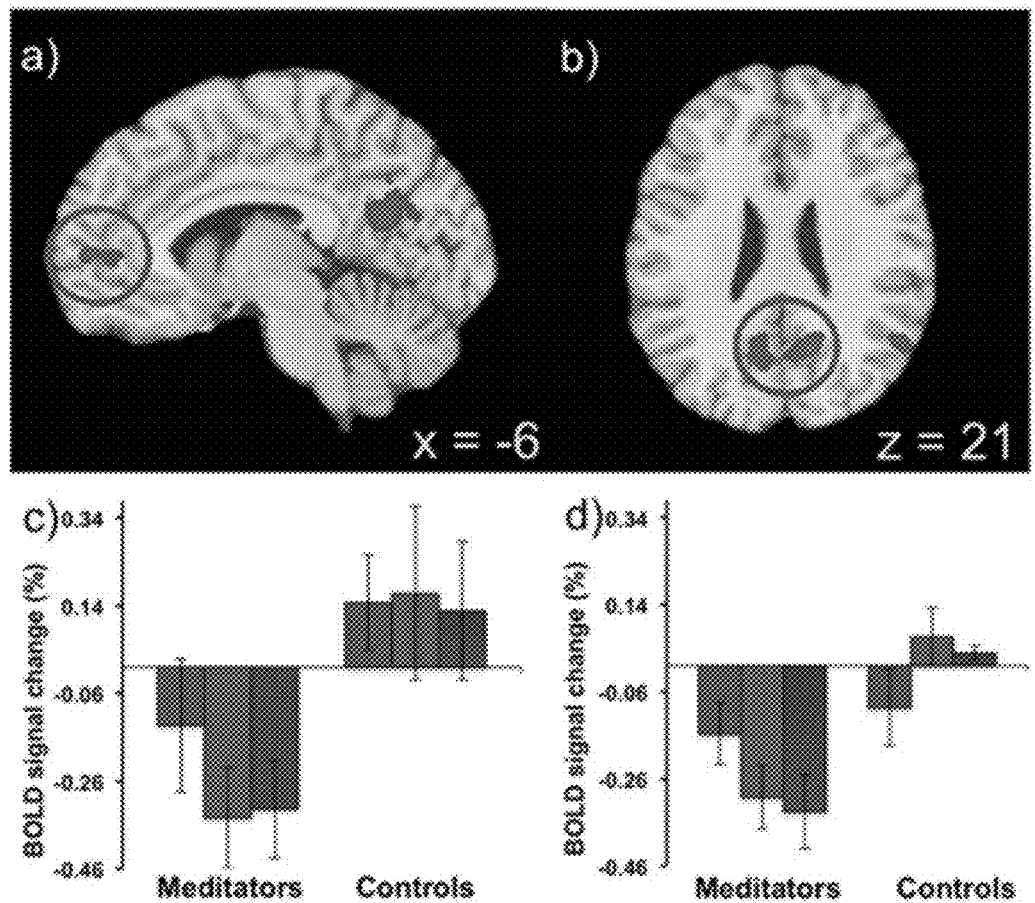
FIG. 1: Experienced meditators demonstrate decreased DMN activation during meditation. Brain activation in meditators>controls is shown, collapsed across all meditations (relative to baseline): (a) and (b) show activations in the left mPFC and PCC; (c) and (d) show average percent signal change (±SD) during individual meditation conditions in the mPFC and PCC respectively: Choiceless Awareness (green bars), Loving-kindness (red), and Concentration (blue) meditations. Note that decreased activation in PCC in meditators is common across different meditation types. N=12/group.

It is to be understood that the figures and descriptions of the present invention have been simplified to illustrate elements that are relevant for a clear understanding of the present invention, while eliminating, for the purpose of clarity, many other elements found in neurofeedback methods and systems. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, is reduced.

The terms "patient," "subject," "individual," and the like are used interchangeably herein, and refer to any animal amenable to the methods described herein. In certain non-limiting embodiments, the patient, subject or individual is a human.

As used herein, "treating a disease or disorder" means reducing the frequency with which a symptom of the disease or disorder is experienced by a patient. Disease and disorder are used interchangeably herein.

The term "visual display" refers to any type of device suitable for the presentation of images. Examples of visual displays include, but are not limited to, light-emitting diode displays (LED), liquid crystal displays (LCD), cathode ray tube displays (CRT), electroluminescent displays (ELD), plasma display panels (PDP), thin-film transistor displays (TFT), electronic paper, holographic projections, and the like.

The term "interactive visual display" refers to any type of device suitable for the presentation of images and also suitable for receiving input. Examples of interactive visual displays include, but are not limited to, tablet computers, touch-screen displays, video game systems, and the like.

The term "meditation" refers to a variety of practices or techniques related to contemplation, reflection, engaging in mental exercise, training the mind, inducing a mode of consciousness, concentration focus, increasing awareness of the present moment, focused thinking, self-regulation of thought, and the like.

The terms "flow state" refers to the mental state of a subject when the subject is performing at the subject's peak without distraction or anxiety, i.e. when the subject is most focused, absorbed, relaxed, creative, and the like.

The terms "fMRI feedback," "rt-fMRI feedback," "fMRI neurofeedback," "rt-fMRI neurofeedback," and the like are used interchangeably herein, and refer to the use of a functional Magnetic Resonance Imaging device to display or provide a representation of a subject's brain activity to the subject in a real-time or substantially simultaneous manner.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, 6 and any whole and partial increments therebetween. This applies regardless of the breadth of the range.

DESCRIPTION

The system and methods of the present invention are based on the finding that the main nodes of the default mode network (DMN) (medial prefrontal and posterior cingulate cortices) are relatively deactivated in experienced meditators, across all meditation types. Further, functional connectivity analysis demonstrates that there is a stronger coupling in experienced meditators between the posterior cingulate, dorsal anterior cingulate and dorsolateral prefrontal cortices (regions previously implicated in self-monitoring and cognitive control), both at baseline and during meditation. Due to differences found in the default mode network that are consistent with decreased mind-wandering, the present invention provides new insight into the neural mechanisms of meditation, including meditation training, control and therapeutic uses thereof.

The present invention further includes systems and methods of using real-time fMRI neurofeedback to improve the correspondence between first-person experience and specific brain activation patterns in a manner that minimally affects the experience itself. The present invention also provides meditators the ability to enhance their control over their own brain activity, such as PCC activation. The present invention provides a system and method of using fMRI neurofeedback to directly correlate subjective experience with neural activation.

As contemplated herein, the system and methods of the present invention can use any sort of brain activity imaging hardware and software, including functional magnetic resonance imaging, source-localized electroencephalography, or by other means understood by those skilled in the art. Furthermore, neurofeedback data can be integrated and presented to the measured subject via any sort of visual, audio or other sensory mechanism, as would be understood by those skilled in the art. Non-limiting examples include a visual display, an interactive visual display (e.g., video game), an auditory signal, or a tactile signal. Information can further be streamed to the subject, if desired.

While the disclosure herein focuses on the DMN, and particularly the PCC, the present invention is suitable for use with any area or region of the brain, including without limitation, the dorsal anterior cingulate, dorsolateral prefrontal cortex, posterior parietal cortex, posterior insula and thalamus.

As contemplated herein, the present invention includes systems and methods for alleviating and/or treating a disease or disorder. Non-limiting examples of the types of treatable diseases or disorders may include ADHD, Alzheimer's disease, stress-related diseases and disorders, mind-wandering, depression, mood disorders, substance use disorders, autism, schizophrenia, and the like.

As contemplated herein, the present invention provides a real-time neurofeedback mechanism to assist a subject to obtain, maintain, optimize and/or enhance a meditative state or "flow" state. Such states are conducive to the reduction of disorders or diseases, or the treatment of such symptoms or conditions as described herein. The present invention provides a platform for a subject to obtain, maintain, optimize and/or enhance a meditative state or "flow" state via the instruction provided by the feedback system in real-time. This instruction provides the subject the opportunity to augment or alter their meditative state to obtain the desired brain activity presented to them in real time.

Thus, the present invention includes a method of enhancing a meditative state of a subject. The method includes the steps of measuring a subject's PCC activity by fMRI, presenting a representation of the subject's PCC activity to the subject simultaneously with said measuring, and instructing the subject to alter their meditative state, such that the alteration to their meditative state decreases PCC activity. In one embodiment, the enhanced meditative state reduces mind-wandering. In another embodiment, the enhanced meditative state reduces stress.

The present invention also includes a method of treating a disease or disorder of a subject. The method includes the steps of measuring a subject's PCC activity by fMRI, presenting a representation of the subject's PCC activity to the subject simultaneously with said measuring, instructing the subject to enter into a meditative state, and instructing the subject to reduce the represented PCC activity by optimizing their present meditative state. In one embodiment, the disease is Alzheimer's disease. In another embodiment, the disorder is ADHD. In one embodiment, the disorder is stress-related. In one embodiment, the disorder is mind-wandering.

The present invention also includes a method of correlating a subject's subjective report to at least one neuronal process of the subject. The method includes the steps of measuring a subject's PCC activity by fMRI, presenting a representation of the subject's PCC activity to the subject simultaneously with said measuring, and instructing the subject to provide a report of their mental state when viewing the presented representation of the subject's PCC activity. In another embodiment, the representation presented is via a visual display, an interactive visual display, an auditory signal, or a tactile signal. The present invention also includes a method of correlating information of a subject with a neuronal process of the subject, including the steps of detecting levels of brain activity of a subject from at least one of the following specific brain regions in a human subject: posterior cingulate cortex, dorsal anterior cingulate, dorsolateral prefrontal cortex, posterior parietal cortex, posterior insula, thalamus, and correlating the detected level of activity with the subject's physiological stress level/indicator(s), degree of self-referential activation, depth of meditation, depth of "flow" state occurring at substantially the same time as the detected brain activity. In one embodiment, the detecting is performed by fMRI or source-localized electroencephalography.

The systems or methods of the present invention can also include simultaneously measuring the subject's brain activity in more than one brain region and presenting a representation of each of the subject's measured brain activities to the subject simultaneously to said measuring.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the descriptions and the illustrative examples hereinthroughout, practice the present invention. The following examples therefore, are not to be construed as limiting in any way the remainder of the disclosure.

Example 1: Meditation Experience is Associated with Differences in DMN Activity and Connectivity As contemplated herein, it was hypothesized that the DMN would be an important locus of change following meditation training. Specifically, it is believed that brain activation during mindfulness meditation in experienced meditators as compared to their matched controls would involve (1) relatively reduced recruitment of the DMN, and (2) relatively increased connectivity between DMN and brain structures that are implicated in monitoring for conflict as well as cognitive control, such as the dorsal anterior cingulate (dACC), and dorsolateral prefrontal cortices (dlPFC) respectively. To test this, fMRI was used to assess brain activation during both a resting state and a meditation period in experienced mindfulness meditation practitioners and controls. To determine common neural activation patterns across meditations, participants were scanned during periods of Concentration, Loving-kindness, and Choiceless Awareness meditation.

The following methods were used in experimental example 1:

Subjects

Twelve right-handed individuals with >10 years and an average of 10565±5148 hours of mindfulness meditation experience, and thirteen healthy volunteers were recruited to participate. Right-handed meditation-naïve controls were case-control matched for country of origin (US), primary language (English), gender, age, race, education, and employment status. One control participant did not follow directions and was removed before any analyses were performed. With the exception of a single mismatch in gender and age respectively, all participants were well-matched (e.g. within 3 years of age of their match). All participants gave informed consent in accordance with the procedures of the Yale University Human Investigation Committee.

Task

Just prior to scanning, all participants were introduced to three standard mindfulness meditation instructions: 1) Concentration: "please pay attention to the physical sensation of the breath wherever you feel it most strongly in the body. Follow the natural and spontaneous movement of the breath, not trying to change it in any way. Just pay attention to it. If you find that your attention has wandered to something else, gently but firmly bring it back to the physical sensation of the breath."; 2) Loving-kindness: "please think of a time when you genuinely wished someone well (pause). Using this feeling as a focus, silently wish all beings well, by repeating a few short phrases of your choosing over and over. For example: May all beings be happy, may all beings be healthy, may all beings be safe from harm."; and 3) Choiceless Awareness: "please pay attention to whatever comes into your awareness, whether it is a thought, emotion, or body sensation. Just follow it until something else comes into your awareness, not trying to hold onto it or change it in any way. When something else comes into your awareness, just pay attention to it until the next thing comes along." Participants practiced each meditation type outside of the scanner and confirmed that they understood and could follow the instructions before proceeding. Each run began with a 2-minute resting-state baseline period ("please close your eyes and don't think of anything in particular"), which is consistent with standard resting-state induction procedures (Raichle et al., 2001, Proc. Natl. Acad. Sci. USA 98(2):676; Castellanos et al., 2008, Biol. Psychiatry 63(3): 332-337; Fox et al., 2005, Proc Natl Acad Sci USA 102(27): 9673-9678). This was followed by a 30-second recorded meditation instruction (as above), and a 4.5-minute meditation period. Every subject performed each meditation twice. Meditation conditions were presented in a random order, but the second instance of each meditation was blocked (i.e. AABBCC). After each run, participants were asked to rate how well they were able to follow the instructions and how much their mind wandered during each meditation period on a scale of 0-10.

Statistical Analysis of Self-Report Data

Multivariate analysis was performed of variance (MANOVA) using SPSS 18 (SPSS, Inc; Chicago, Ill.). All tests of significance are reported as two-tailed, and means are reported with ±standard deviation.

Imaging Data Acquisition

Functional and structural data were acquired on a 3T TRIO Siemens MRI scanner (Siemens Healthcare, Erlangen, Germany) located at Yale's Magnetic Resonance Research Center. A high resolution, 3-D Magnetization Prepared Rapid Acquisition Gradient Echo (MPRAGE) T1-weighted sequence was used to acquire anatomical images (TR=2530 ms; echo time (TE)=3.66 ms; Flip angle=7 degrees; Field of view=256×256 mm; Matrix=256× 256); and 176 1 mm slices). Blood Oxygen Level Dependent (BOLD) functional images were acquired with a T2*-sensitive echo-planar image (EPI) gradient-echo pulse sequence (TR=2000 ms; TE=25 ms; Flip angle: 85 degrees; Field of view=220×220 mm; Matrix=64×64; and 32 4 mm slices). Each functional run consisted of 210 volumes, including an initial rest period of 10 seconds (to achieve signal stability) that was removed from the data prior to preprocessing.

Imaging Data Processing

Functional images were subjected to standard preprocessing using SPM5 (Wellcome Department of Cognitive Neurology) following prior published methods (e.g. Kober et al., 2010, Proc Natl Acad Sci USA 107(33):14811-14816). This included the following steps: slice scan-time correction to the middle slice of each volume; a two-pass realignment of all functional images, first to the first image of the first functional scan, and then to an interim computed mean image; co-registration of the anatomical image and the average of these realigned functional images; co-registration of all functional images using the parameters obtained from co-registration of the mean image; application of the SPM Unified Segmentation process to the anatomical scan, using prior information from the ICBM Tissue Probabilistic Atlas and estimation of non-linear warping parameters (Ashburner & Friston, 2005, Neuroimage 26(3):839-851); warping the functional images to the Montreal Neurological Institute (MNI) template space, followed by smoothing of functional images using a 6 mm isometric Gaussian kernel.

GLM Data Analysis

First-level robust regression was performed on each participant's preprocessed images, using the standard general linear model but with iteratively reweighted least squares using the bisquare weighting function for robustness (Kober et al., 2010, Proc Natl Acad Sci USA 107(33):14811-14816; Wager et al., 2005, Neuroimage 26(1):99-113), as implemented in MATLAB 7.3 (Mathworks, Natick, Mass.; robust.m), using scripts created by H. Kober and J. Weber. Motion parameters and high-pass filter parameters were added as additional regressors of no interest. Activity during each meditation epoch was estimated as percent signal change from resting baseline. Next, a second-level, random effects analysis was performed to estimate group activity during each meditation epoch, and to compare activity between groups, using NeuroElf (NeuroElf net). Results are FamilyWise Error corrected for multiple comparisons at $p<0.05$ unless otherwise indicated.

Functional Connectivity Analysis: Region-of-Interest Definition

To assess the connectivity of brain regions with the DMN, two regions of interest (ROIs) were defined in mPFC and PCC (MNI coordinates −6, 52, −2 and −8, −56, 26 respectively), based on DMN coordinates reported previously (e.g. Andrews-Hanna et al., 2010, Neuron 65(4):550-562). Given that these were located very close to the midplane (X=0) right and left mPFC and PCC were combined respectively by selecting all voxels within a sphere of 10 mm radius around coordinates projected orthogonally onto the midplane (X=0) of the brain.

Definition of Temporal Segments of Interest

To determine differences in network connectivity, three temporal epochs of 50 volumes/100 seconds each, were defined as follows: 1) resting-state baseline ("please close your eyes and don't think of anything in particular"—the epoch prior to the instruction to meditate; volumes 6 through 55), 2) an initial meditation phase (immediately following the instruction; volumes 76-125) and 3) a later meditation phase (at the end of each of the meditation sessions; volumes 158-207). For each of these segments, seed-correlations were then computed.

ROI Time-Course Preparation

For each of the six meditation sessions (3 types with one repetition each), the average time course of the regions of interest (ROIs) was extracted for the three different 50-volume/100-second segments. To ensure that maps representing the covariance (correlation) between regions and other brain areas were as unbiased as possible towards spurious positive correlation, the average time course of all white-matter (WM) voxels was also extracted. White matter is typically considered to not show any BOLD-related changes, so that any signal variation in these areas is usually attributed to noise components. Therefore, the ROI time courses were orthogonalized against this WM time course.

Generation of First-Level Seed-Correlation Maps

To assess connectivity and between-group differences, separate multiple linear regression models were computed for each of the segment-by-ROI pairs. The models contained the ROI time course as covariate of interest and the respective WM time course as covariate of no interest (to account for fluctuations most likely driven by global signal changes). For each of these models a z-map was computed, reflecting the z-score in each voxel assessing the likelihood of signal changes being correlated to the seed under the null hypothesis. The two homonymous maps (stemming from the two segments of equal meditation technique, e.g. early meditation for the two Loving-kindness runs) were combined using Stouffer's z method. The rationale behind this approach is that under the null hypothesis (no effect for simple tests and no differential effect for task-difference tests) this measure is normally distributed around 0, a pre-requisite for subsequent second-level analyses.

Second-Level Random-Effects Statistical Analysis

Using these correlation maps (the initial 9 maps per subject, based on 3 meditation types and 3 parts of the timecourses-baseline, early, and late meditation-which were condensed into 6 maps, whereas the early and late correlation maps were combined using the Stouffer z method), we computed between group differences for the three meditation types.

As expected, experienced meditators reported less mind-wandering during meditation relative to controls ($F_{(1,22)}$= 7.93, p=0.010). This was apparent for Concentration (controls=4.9±2.9, meditators=3.2±1.3), Loving-kindness (controls=5.0±2.8, meditators=3.2±1.3), and Choiceless Awareness meditation (controls=6.0±3.1, meditators=3.4±1.5). Across groups, there was also an effect of time ($F_{(1,22)}$=5.01, p=0.036), such that reported mind-wandering was greater during the second run of each meditation condition (Time 1=4.08±1.9, Time 2=4.48±2.16). Both meditators and controls reported being able to follow the instructions to a high degree for the Concentration (controls=7.5±2.3, meditators=8.1±1.2), Loving-kindness (controls=7.5±2.6, meditators=7.8±1.5), and Choiceless Awareness meditation conditions (controls=8.5±2.0, meditators=7.9±1.3).

To test the hypothesis that meditators would show differential changes in brain activation during meditation relative to controls, a between-groups whole-brain contrast analysis collapsing across the three meditation conditions was performed. It was found that relatively less activation in meditators compared to controls in the PCC, a primary node of the DMN, as well as the superior, middle and medial temporal gyri and uncus (FIG. 1). Also found was a similar pattern in the medial prefrontal cortex (mPFC), another primary node of the DMN, though it did not survive whole brain correction for significance (cluster size k=33, threshold k=43; FIG. 1).

Figure 2:
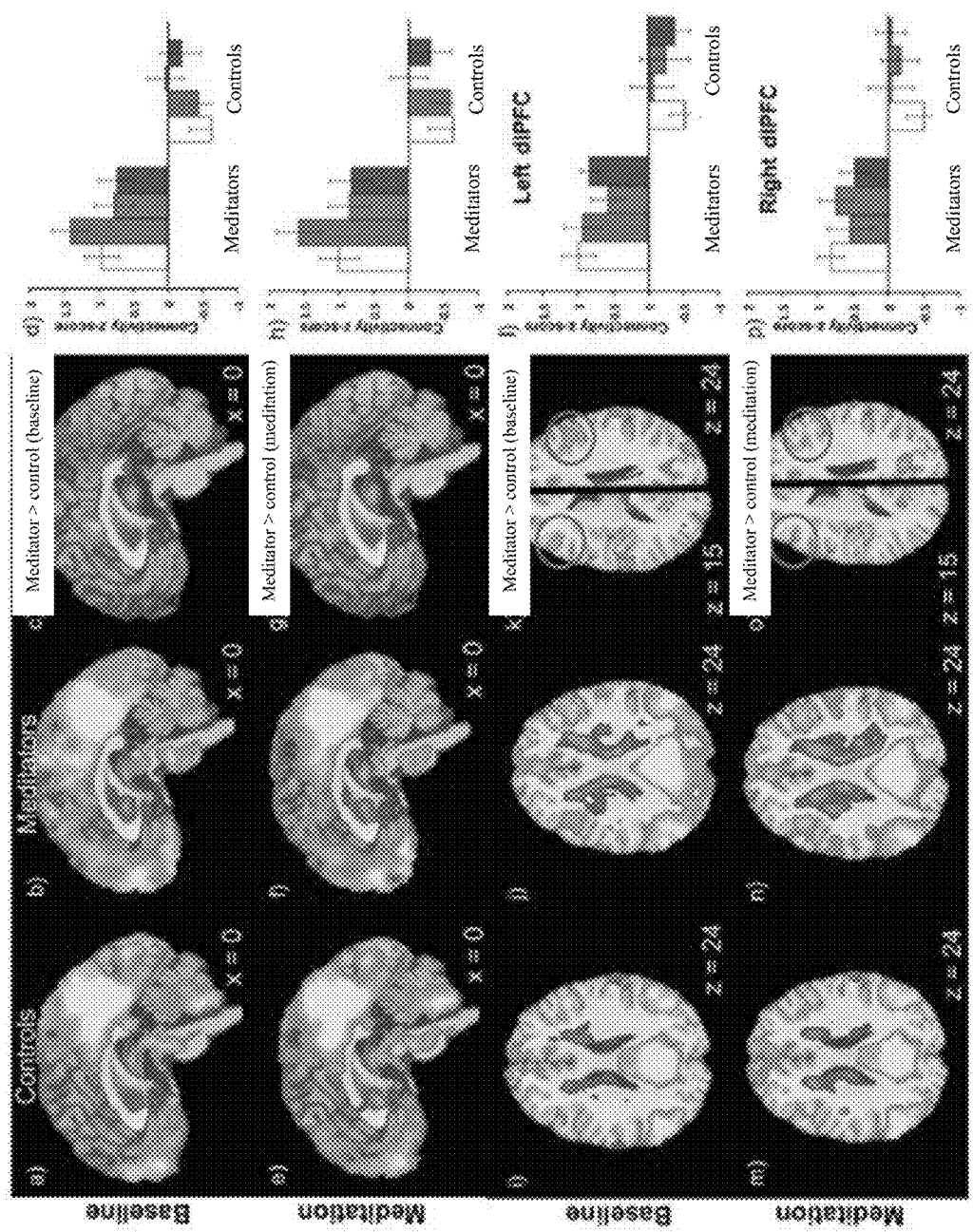
FIG. 2: Experienced meditators demonstrate co-activation of PCC, dACC, and dlPFC at baseline and during meditation. Functional connectivity with the PCC seed region collapsed across all meditation conditions, is shown in (a, i) controls at baseline; (b, j) meditators at baseline (c, k) meditators>controls at baseline; (e, m) controls during meditation; (f, n) meditators during meditation; (g, o) meditators>controls during meditation. Connectivity z-scores (±SD) are shown in (d) for dACC cluster from panel c; (h) for dACC cluster from panel g; (l) for left dlPFC cluster from panel k; and (p) for right dlPFC cluster from panel k. Baseline (white bars), Choiceless Awareness (green bars), Loving-kindness (red bars), and Concentration (blue bars) meditation conditions are shown separately for meditators (left) and controls (right). N=12/group. FWE corrected, p<0.05.

Next, between-group differences in each meditation condition were examined. During the Concentration meditation condition, there was relatively less activation in meditators in the PCC, and left angular gyrs (FIG. 1d, 2a-b) as compared to controls. During Loving-kindness meditation, there was relatively less activation in meditators as compared to controls in the PCC, inferior parietal lobule, and inferior temporal gyrs extending into the hippocampal formations, amygdala, and uncus (FIG. 1d, 2c-d). During Choiceless Awareness, there was relatively less activation observed in meditators as compared to controls in the superior and medial temporal gyrs.

To test the hypothesis that meditators co-activate different brain regions compared to controls when nodes of the DMN become activated, functional connectivity analyses were performed during both baseline and meditation periods, using a priori defined DMN seed regions from the mPFC and PCC (MNI coordinates −6, 52, −2 and −8, −56, 26 respectively) (7). Using the PCC as the seed region, across all meditation conditions significant differences were found in connectivity patterns with several regions, notably the dACC, (FIG. 2e-h). This pattern of differential between-group connectivity held during the resting-state baseline period as well, suggesting a stable pattern of connectivity regardless of task (resting-state baseline vs. meditation, FIG. 3a-d). A similar connectivity pattern was found between the PCC and dlPFC at baseline (FIG. 2i-l) that was not significantly different between groups during meditation due to a relatively lower strength of anti-correlations in controls (FIG. 2m-p).

Figure 3:
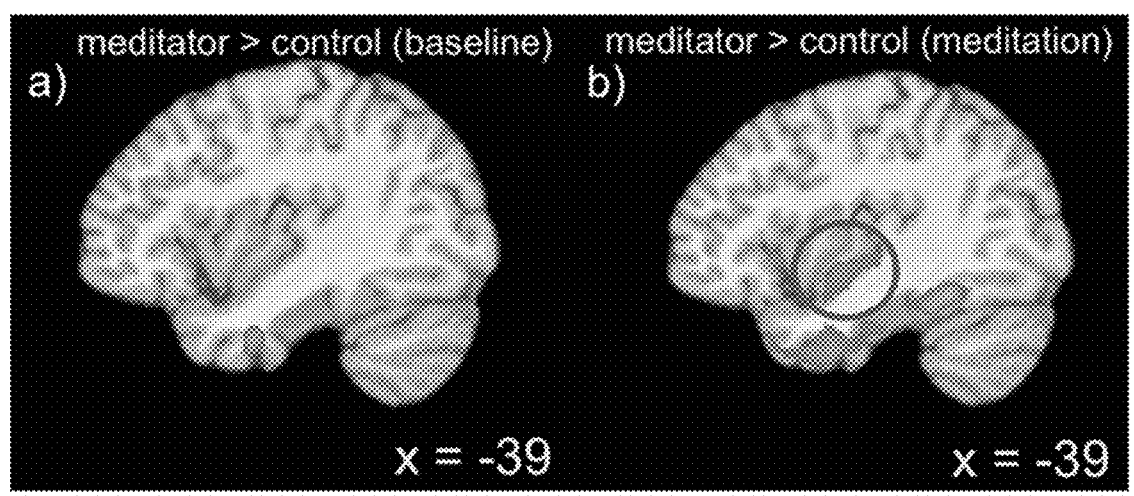
FIG. 3: Experienced meditators demonstrate co-activation of mPFC, insula and temporal lobes during meditation. Differential functional connectivity with mPFC seed region and left posterior insula is shown in meditators>controls: (a) at baseline and (b) during meditation. Connectivity z-scores (±SD) are shown for left posterior insula in (c). Choiceless Awareness (green bars), Loving-kindness (red), and Concentration (blue) meditation conditions are shown separately. For each color, baseline condition is displayed on the left and the meditation period on right. N=12/group. FWE corrected, p<0.05.

Using the mPFC as the seed region, increased connectivity with the fusiform gyrs, inferior temporal and parahippocampal gyri, and left posterior insula (among other regions) in meditators relative to controls during meditation was found (FIG. 3a-c). A subset of those regions showed the same relatively increased connectivity in meditators during the baseline period as well.

As predicted, across all mindfulness meditation conditions, the two primary nodes of the DMN (the PCC and mPFC) were less active in meditators than controls. Also observed were meditation-specific regional differences in activation patterns, such as deactivation in the amygdala during Loving-kindness. Finally, using DMN seed regions, distinct functional connectivity patterns were observed in meditators that differed from controls, and which were consistent across resting-state baseline and meditation conditions. These results suggest that the neural mechanisms underlying mindfulness training are associated with differential activation and connectivity of the DMN. As meditators also reported significantly less mind-wandering, which has been previously associated with activity in DMN, these results support the hypothesis that alterations in DMN are related to reduction in mind-wandering. Finally, the consistency of connectivity across both meditation and baseline periods suggests that meditation practice may transform the resting-state experience into one that resembles a meditative state, and as such, is a more present-centered default mode.

The meditation sample was restricted to very experienced meditators from a single practice tradition (mindfulness/insight meditation). This was intended to reduce heterogeneity in meditation practices. Additional strengths of the study include the use of three standardized meditation techniques that are taught within this tradition, and the utilization of control subjects that were case-matched for a number of demographic parameters. This kind of matching increases the likelihood of yielding results that are both valid and generalizable to individuals in the western hemisphere. Furthermore, because experienced meditators train to be mindfully aware all of the time, and thus may be activating similar brain regions during both resting-state and meditation, GLM analyses may be limited due to their dependence upon a relative change from baseline. Therefore, functional connectivity was employed as a complementary analytic technique within a single data set. This convergent analysis directly addresses the limitations of baseline conditions in previous studies.

From a theoretical perspective, the view of meditation as consisting of training away from mind-wandering and self-identification gave rise to several predictions that were confirmed by the data. First, given the primacy of the DMN in self-referential processing and mind-wandering, the primary prediction was that the DMN would be the main "target" of meditation practice, and that alterations in classic DMN activity would be found in experienced meditators relative to controls. Indeed, though not consistently, prior work has suggested alterations in DMN following brief meditation training and in experienced meditators. For example, consistent with previous reports of PCC activation during 'selfing' tasks, Pagnoni and colleagues showed relative activation in the PCC in Zen meditators+controls when viewing words vs. scrambled non-word letters while meditating, though no between-group differences were found. Further, Farb and colleagues reported that individuals who had received eight weeks of MBSR demonstrated relative deactivation of the PCC when performing a task in which they engaged in awareness of thoughts, feelings and body sensations when reading personality-train adjectives, compared to determining what the words meant to them personally. However, to date no studies have reported alterations in DMN activation or functional connectivity during meditation itself. Clarifying this prior work, the data presented herein is novel in that they provide direct evidence for this prediction, as meditators showed relatively decreased activation in mPFC and PCC, the two primary nodes of the DMN during meditation. This finding is especially salient as meditators reported significantly less mind-wandering during meditation periods relative to controls. Taken together, and inasmuch as activity in DMN regions reflects self-referential processing and mind-wandering, the current data suggest that meditators are engaged in these processes less than their control counterparts.

A second prediction that emerged from the view of mindfulness as a task of monitoring and letting go of self-referential thought to keep present-focused attention, was that experienced meditators would be more likely to activate "task positive" brain regions such as those implicated in conflict monitoring, working memory and cognitive control. However, as noted above, it was believed that this may be due to the dependence of GLM analysis on activity during baseline. The baseline-independent functional connectivity analyses directly addressed this confound. It was found that relative to controls, meditators showed increased connectivity between PCC and task-positive regions, during resting-state baseline and all meditation conditions, including those involved in conflict monitoring, cognitive control, and working memory (dACC and dlPFC). These findings suggest that meditators may be on-task regardless of condition, which also provides a possible explanation for the relative paucity of between-group differences that were observed with GLM analyses. Importantly, this increased connectivity with the dACC and dlPFC was not seen using the mPFC as the seed region, which is consistent with the purported role of the mPFC in integrating information gathered from the internal and external environment and relaying it to the PCC, rather than being directly involved in self-related processing. Interestingly, a study using independent component analysis to assess functional connectivity during a "mindful awareness" scan after an eight-week MBSR course was recently reported (Kilpatrick et al., 2011, Neuroimage 56(1):290-298). Similar to the mPFC seed-region results presented herein, Kilpatrick et al. found increased connectivity between the mPFC and primary interoceptive awareness regions including the posterior insula. However, Kilpatrick et al. did not find increased connectivity with other DMN regions, such as the PCC. Several possible explanations for this include 1) the use of different analytic tools (ICA vs. a PCC seed region for connectivity analysis) 2) the brief duration of meditation training (eight weeks), and 3) the specific emphasis on mindful awareness of sounds in the task instructions, among others.

Though direct links between white matter tract integrity (e.g. diffusion tensor imaging), brain volume, and functional connectivity are just beginning to be established, several recent studies of meditation using these measures may support our findings. For example, Tang and colleagues showed improved white matter tract integrity in the vACC and dACC after just 11 hours of Integrative Body-Mind Training meditation (Tang et al., 2010, Proc Natl Acad Sci USA 107(35):15649-15652). Also, Luders et al. found increased white matter integrity in dACC, among others in experienced meditators compared to controls (Luders et al., 2011, Neuroimage 57(4):1308-1316). Regarding gray matter density, in an exploratory analysis of individuals who had received MBSR, Holzel and colleagues found increased gray matter concentration in the PCC. (Holzel, 2011, Psychiatry Res 191(1):36-43) Also, Luders et al. found increased gray matter concentration in the inferior temporal gyms in experienced meditators (Luders et al., 2009, Neuroimage 45(3):672-8). Taken together, these studies of neuronal integrity and brain concentration may corroborate the findings herein, as these regions were shown to have increased connectivity in the present study.

The findings from this study support the default-mode interference hypothesis, which states that the DMN can persist or reemerge during goal-directed tasks "to such an extent that it competes with task-specific neural processing and creates the context for periodic attentional intrusions/lapses and cyclical deficits in performance". This hypothesis has been built from observations of decreased activity in the task-positive network and increased activity in the DMN during mindlessness. It has been further supported by the demonstration that stimulant (nicotine) administration enhances attention by deactivating areas of the DMN such as the PCC. More importantly, pathological states have shown altered DMN connectivity and anti-correlations with the task-positive network. However, no studies have shown convergence of the two networks, in states of well-being or otherwise. With fewer reported attentional lapses, decreased mPFC and PCC activation during meditation and increased connectivity patterns between DMN and self-control regions of the brain, the data presented herein provides corollary support for the interference hypothesis. Moreover, functional connectivity data herein suggest that meditation practice may couple primary nodes of these networks in a potentially beneficial way—temporally linking the PCC to monitoring and self-control regions such that when regions of the DMN emerge to "interfere" with a task, control regions may co-activate to monitor and/or dampen this process. This co-activation of monitoring/control regions along with nodes of the DMN may, over time, become a new 'default mode' that can be observed during resting-state as well as during meditation.

Finally, the findings from this study have several clinical implications, as a number of pathological conditions have been linked to dysfunction within areas of the DMN. For example, ADHD is characterized by attentional lapses. The majority of research on the pathophysiology of ADHD has centered on frontal-striatal circuitry, but recent studies have begun to explore other mechanisms including activity in, and connectivity with nodes of the DMN. In particular, Castellanos and colleagues found decreases in anti-correlations between the PCC and dACC in individuals with ADHD. Individuals who have undergone mindfulness training, during which they try to minimize attentional lapses, may be an interesting contrast to those with ADHD. Indeed, mindfulness training has shown preliminary efficacy in treating this disorder, but how it affects brain function in individuals with ADHD remains unknown. The data presented herein demonstrates that mindfulness may help to enhance PCC-dACC connectivity in individuals with ADHD, which may correlate with reduced attentional lapses. Another pathological condition that has been linked to DMN activity is Alzheimer's disease. Sustained neuronal activity has recently been linked to increased amyloid-[beta] deposition, potentially explaining the connection between prolonged metabolic activation in the DMN and Alzheimer's, as well as the links between education levels and delay of onset. Results from the present study suggest that meditation is a way to decrease DMN activity in a relatively specific manner, using simple instructions and at low cost. As such, meditation may also bring with it the advantage of being accessible to many individuals regardless of educational and economic background. Meditation may also be a way to delay the onset of Alzheimer's disease. Without limitation to particular clinical implications, the findings herein demonstrate group differences in the DMN that are consistent with a decrease in mind-wandering in experienced meditators, and provide a basis for a new understanding of the neural bases of mindfulness meditation practice.

Example 2: First-Person Experience of Mind-Wandering Correlate with Increased PCC Activation, and Meditation Correlates with Decreased Activation in this Brain Region In the following experimental example, rt-fMRI neurofeedback is used to test the feasibility of linking subjective self-report of a meditative state to neural activity in the PCC. The PCC is selected for several reasons. First, it has been implicated as a central node of the DMN. Second, the PCC is specifically and robustly deactivated during different types of meditation. In is hypothesized that individual reports of first-person experience of mind-wandering or other types of self-referential activity would correlate with increased PCC activation and that meditation would correlate with decreased activation in this brain region. Further, it was hypothesized that individuals would be able to discriminate between PCC activity and activity in the posterior parietal cortex, a region in the DMN that is tightly temporally coupled to the PCC but has not been strongly correlated with self-referential thoughts.

The following methods were used in experimental example 2:

Subjects 22 right-handed experienced meditators and 22 matched novice controls were recruited to participate. Meditators reported on average 13.9±7.9 years and 9249±6799 hours of mindfulness meditation experience (one meditator practiced both mindfulness and non-dual meditation as primary practices). Right-handed meditation-naïve controls were case-control matched for gender, age, race, education, and employment status (see Table 1). All participants gave informed consent in accordance with the procedures of the Yale University Human Investigation Committee.

TABLE 1

Table 1. Baseline characteristics of participants

| | MED (n = 22) | CONT (n = 22) | Total (n = 44) | For $\chi^2$ | df | p |
|---|---|---|---|---|---|---|
| Sex | N (%) | N (%) | N (%) | 0 | 1 | 1 |
|   Male | 13 (59.1) | 13 (59.1) | 26 (59.1) | | | |
|   Female | 9 (40.9) | 9 (40.9) | 18 (40.9) | | | |
| Age | 44.7 ± 12.6 | 42.9 ± 13.8 | 43.8 ± 13.1 | 0.185 | 1 | 0.67 |
| Race | | | | | | |
|   White | 22 (100) | 22 (100) | 44 (100) | N/A | | |
| Education level | | | | 5.451 | 3 | 0.142 |
|   Completed graduate/prof training | 14 (63.6) | 11 (50.0) | 25 (56.8) | | | |
|   College grad | 5 (22.7) | 6 (27.3) | 11 (25.0) | | | |
|   Partial college | 3 (13.6) | 1 (4.5) | 4 (9.1) | | | |
|   High School | 0 | 4 (18.2) | 4 (9.1) | | | |
| Years of Education | 17.9 ± 3.1 | 16.6 ± 3.4 | 17.3 ± 3.3 | 1.852 | 1 | 0.181 |

Task

Figure 4:
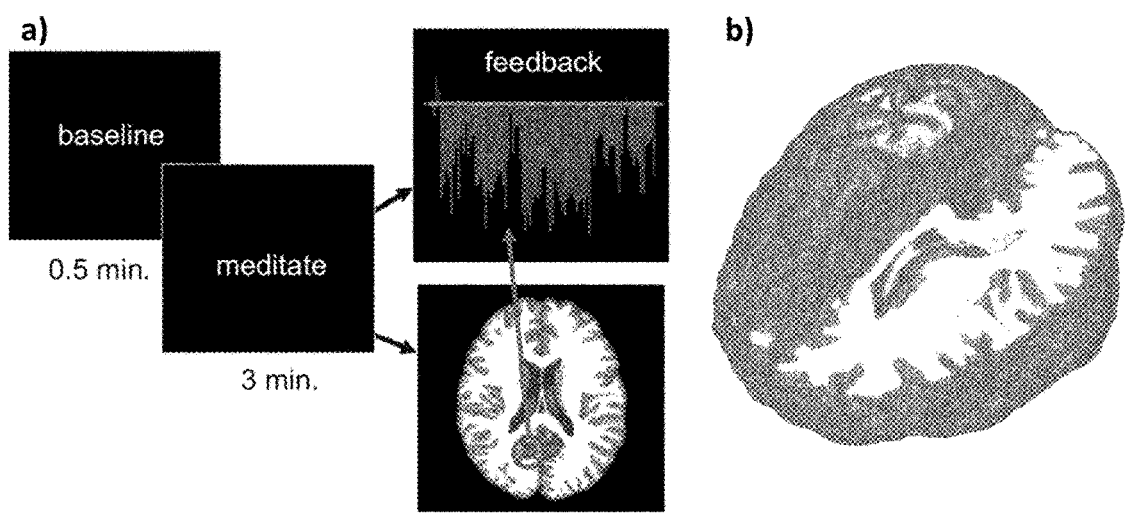
FIG. 4: Schematic of rt-fMRI neurofeedback. a) Individuals performed a 0.5 min baseline task in which they viewed adjectives and decided if these described them, and then were asked to meditate for 3 minutes with their eyes open while their brain activation in the posterior cingulate cortex (PCC), or posterior parietal cortex control region, was displayed in the background. During meditation, they were instructed to check the graph periodically to determine how well it matched their subjective experience. b) Regions of interest: PCC (red, MNI coordinates: −6, −60, 18), posterior parietal cortex (yellow, MNI coordinates: −55, −51, 19), and remaining grey matter (light blue).

Each study run consisted of collecting a 30-second active baseline in which individuals viewed adjectives and mentally decided whether or not the words described them (Kelley, et al., 2002, J Cogn Neurosci 14(5):785-794), followed by a 3-minute meditation period in which a graph depicting BOLD percent signal change relative to the average activation from the baseline period in either the PCC or the posterior parietal cortex (control region), was displayed to the subject (see FIG. 4a). An active baseline condition was used to provide a relatively more standard baseline signal, as it has been argued and recently shown that experienced meditators may adopt a more meditative stance during a passive baseline (Holzel, et al., 2007, Neuroscience Letters 421(1):16-21; Brewer, et al., 2011, Proc Natl Acad Sci USA 108(50):20254-9). The PCC was chosen as an a priori region of interest due to recent findings showing it's activation during self-referential processing (Kelley, et al., 2002, J Cogn Neurosci 14(5):785-794; Northoff, et al., 2006, NeuroImage 31(1):440-457; Weissman, et al., 2006, Nat Neurosci 9(7):971-978; Mason, et al., 2007, Science 315 (5810):393), and, importantly, because it is a common area of deactivation during different types of meditation. The posterior parietal cortex was used as a control region as it is a major node of the DMN that has been shown not to correlate as strongly with self-referential processing as the PCC (Northoff & Bermpohl, 2004, Trends in Cognitive Sciences 8(3):102; Northoff, et al., 2006, NeuroImage 31(1): 440-457; Andrews-Hanna et al., 2010, Neuron 65(4):550-562). Thus, in theory, the posterior parietal cortex should show similar patterns of activity to the PCC, but its activity should not correlate as well with subjective reports.

Participants were instructed to meditate with their eyes open, as is standard in many meditative traditions (instructions below), letting the graph of BOLD percent signal change stay in the background or off to the side of their awareness, and, from time to time, to check the graph to see if it correlated with their experience. Participants were instructed that they would be receiving feedback from a brain region that was thought to be involved in self-referential processing and that increased (red) signal on the graph reflected self-referential processing (examples of which were mind-wandering, trying to win something or thinking about what they are going to do later), and decreased (blue) signal reflected meditation. They were educated to the fact that, due to the nature of fMRI signal (i.e. the hemodynamic response function has been shown to have a time lag that peaks between 4-8 seconds after neuronal activation (Lee, et al., 2005, Appl Psychophysiol Biofeedback 30(3):195-204; Bandettini, et al., 1993, Magnetic Resonance in Medicine 30(2):161-173), the feedback that they were receiving would show a delay of up to eight seconds from what was happening in their brain. Thus, they were instructed to check the graph particularly after periods of excessive mind-wandering or deep meditation, and then immediately return their attention to meditation. Their aim was only to determine how well their experience correlated with the graph. Participants were also informed that they may receive feedback from different parts of the brain during different runs, and thus should consider each run individually. The graph began displaying values directly after the active baseline period, with an additional value plotted roughly every two seconds, concomitant with each new BOLD frame that was collected (TR=2 seconds). Each subject performed six runs total. Runs five and six were randomized to show feedback from either the PCC or posterior parietal cortex. After each run, participants were asked to rate on a scale of 0-10 how well they were able to follow the instructions and how well their subjective experience of mind-wandering and meditation correlated with the graph. Additionally, they were instructed to briefly describe how they knew that their experience lined up with meditation. Responses were recorded and transcribed. After the 6th run, subjects were informed which of the feedback runs (#5 vs. #6) was from the control region (posterior parietal cortex) of the brain.

Meditation Instructions

All participants were instructed in standard mindfulness concentration meditation, as follows: "Pay attention to the physical sensation of the breath wherever you feel it most strongly in the body. Follow the natural and spontaneous movement of the breath, not trying to change it in any way. Just pay attention to it. If you find that your attention has wandered to something else, gently but firmly bring it back to the physical sensation of the breath" (Gunaratana, H. (2002), Mindfulness in Plain English. Somerville, Mass., Wisdom Publications; Brewer, et al., 2011, Proc Natl Acad Sci USA 108(50):20254-9). Participants practiced meditation outside of the scanner and confirmed that they understood and could follow the instructions before proceeding.

Imaging Data Acquisition and Real-Time Registration

Subjects were scanned in a Siemens 1.5 Tesla Sonata scanner. After a first localizing scan, a high-resolution sagittal scan was collected using a magnetization prepared rapid gradient echo (MPRAGE) sequence (TR=2530 ms, TE=3.34 ms, 160 contiguous sagittal slices, slice thickness 1.2 mm, matrix size 192×192, flip angle=8°). Next, a T1-weighted anatomical scan (TR=500 ms, TE=11 ms, FoV=220 mm, thickness=4 mm thick, gap=1 mm) was collected with 25 AC-PC aligned axial-oblique slices. After these structural images, acquisition of functional data began in the same slice locations as the axial-oblique T1-weighted data. Functional images were acquired using a T2* sensitive gradient-recalled single shot echo-planar pulse sequence (TR=2000 ms, TE=35 ms, flip angle=90, Bandwidth=1446 hz/pixel, matrix size=64×64, FoV=220 mm, interleaved acquisition). Prior to feedback, a short functional series of 10 volumes (first 2 discarded) was collected. This functional series was used as the single subject reference space for motion correction and ROI analysis (see below). Feedback functional runs consisted of 113 volumes with the first two and last volume(s) discarded.

Region of Interest Definition

Gray matter ROIs were defined on a standard template brain (Holmes, et al., 1998, Journal of Computer Assisted Tomography 22(2):324-333) using BioImage Suite (www.bioimagesuite.org). The first 26 ROIs were defined based on prior analysis. Three of these ROIs (the left posterior insula, left PCC, and left posterior parietal cortex) were used for pilot testing of rt-fMRI feedback. The left posterior insula was defined anatomically (volume=2869 mm$^3$) using the Yale Brodmann Atlas (Lacadie, C., R. K. Fulbright, J. Arora, R. T. Constable and X. Papademetris (2008), Brodmann Areas defined in MNI space using a new Tracing Tool in BioImage Suite. Human Brain Mapping (abstract)). The PCC and posterior parietal cortex ROIs were functionally defined. 9 mm diameter spheres (volume=461 mm$^3$) centered at MNI coordinates (−6, −60, 18) for the PCC (local maximum for between-group differences for concentration meditation using GLM analysis) and (−55, −51, 19) for the posterior parietal cortex (significant functional connectivity with PCC in meditators and controls, but no significant activity from GLM analysis). The final ROI consisted of the remaining gray matter that was not included in the previous ROIs (960455 mm$^3$), and was used to control for scanner drift. Feedback displayed to the subjects was only determined from the PCC, posterior parietal, and gray matter drift control ROI. These ROIs are shown in FIG. 4b.

Real-Time Image Processing

Prior to feedback, the ROIs were transformed from template space to single subject reference space through a series of linear and non-linear registrations. Similar to previous studies, a non-linear transformation was first applied to warp the template brain to the individual MPRAGE (3D anatomical) image (Martuzzi, et al., 2010, Neuroimage 49(1):823-834; Hampson, et al., 2011, Brain Connectivity 1(1):91-98). Next, the individual T1 axial-oblique (2D anatomical) image was linearly registered to 3D anatomical image. Finally, the short functional series was linearly registered to the 2D anatomical image. All transformations were visually inspected for accuracy and were estimated using the intensity-only component of the method implemented by BioImage Suite as previously reported (Papademetris, et al., 2001, Med Image Comput Comput Assist Interv. 3216(2004):763-770).

Real-Time fMRI Neurofeedback

The moment-to-moment feedback signal shown to the subject was determined through a series of preprocessing steps for each frame of the fMRI time-series using the rt-fMRI system described previously (Hampson, et al., 2011, Brain Connectivity 1(1):91-98; Scheinost, D., M. Hampson, J. Bhawnani, M. Qiu, R. T. Constable and X. Papademetris (2011). A GPU Accelerated Motion Correction Algorithm for Real-time fMRI. Human Brain Mapping. Quebec City, Canada). Briefly, each slice of an fMRI volume is reconstructed in real-time and each volume is analyzed immediately after acquisition. This analysis includes motion correction, after which the mean activation of in each ROI was calculated for each frame. To account for motion correct and partial volume effects near the edge of the brain, voxels with intensity less than 25% of the overall brain mean were excluded from the calculations of the mean activation. Second, any ROI measurement with greater than a 10% change from the previous frame was treated as an outlier and was replaced by the previous measurement (0th order interpolation). Next, the ROI measurements were temporally smoothed based on the last five values with a zero mean, unit variance Gaussian kernel. Percent signal change in the ROI (either the PCC or posterior parietal cortex) as compared to the ROI average value across the 30 second baseline was corrected for scanner drift by subtracting the percent signal change from the gray matter control region, as previously described (deCharms, et al., 2005, Proc Natl Acad Sci USA 102(51):18626-18631). This corrected ROI measurement was then graphically presented to each subject in real-time (e.g., see FIG. 4a) using E-Prime v. 1.2 (Psychology Software Tools, www.pstnet.com). The entire processing stream from functional volume acquisition to feedback display required less than one second of delay from data acquisition of each new functional brain volume.

Statistical Analysis of Self-Report Data

Statistical analyses were performed using SPSS/PASW 18 (SPSS, Inc; Chicago, Ill.). All tests of significance are two-tailed and means are reported with ±standard deviation.

As expected, all subjects reported success in following the instructions (average scores across all six runs=9.0±0.01). Additionally, individuals reported a high degree of subjective correlation between their first-person experience of self-referential processing correlating with red and meditation correlating with blue (average scores across first four runs=7.5±0.24). These were similar among groups (meditators=7.4±0.16, controls=7.7±0.29).

To determine whether individuals were able to discriminate between feedback derived from signals from the PCC (which was hypothesized to show increased activity during self-referential processing [red] and decreased activity during meditation [blue]) as compared to the parietal cortex), individuals' subjective reports were compared during runs five and six, in which they received feedback from these two regions in a randomized order. As expected, due to the high correlation shown previously between the PCC and posterior parietal cortex in both novices and individuals with meditation experience (Andrews-Hanna, et al., 2010, Neuron 65(4):550-562; Brewer, et al., 2011, Proc Natl Acad Sci USA 108(50):20254-9), correlations of subjective self-reports were relatively high in both regions (PCC=8.1±1.8, posterior parietal cortex=6.9±2.5); however, correlations between subjective experience and feedback from the PCC were significantly higher than those with the posterior parietal cortex ($t_{42}$=3.1, p=0.004).

Figure 5:
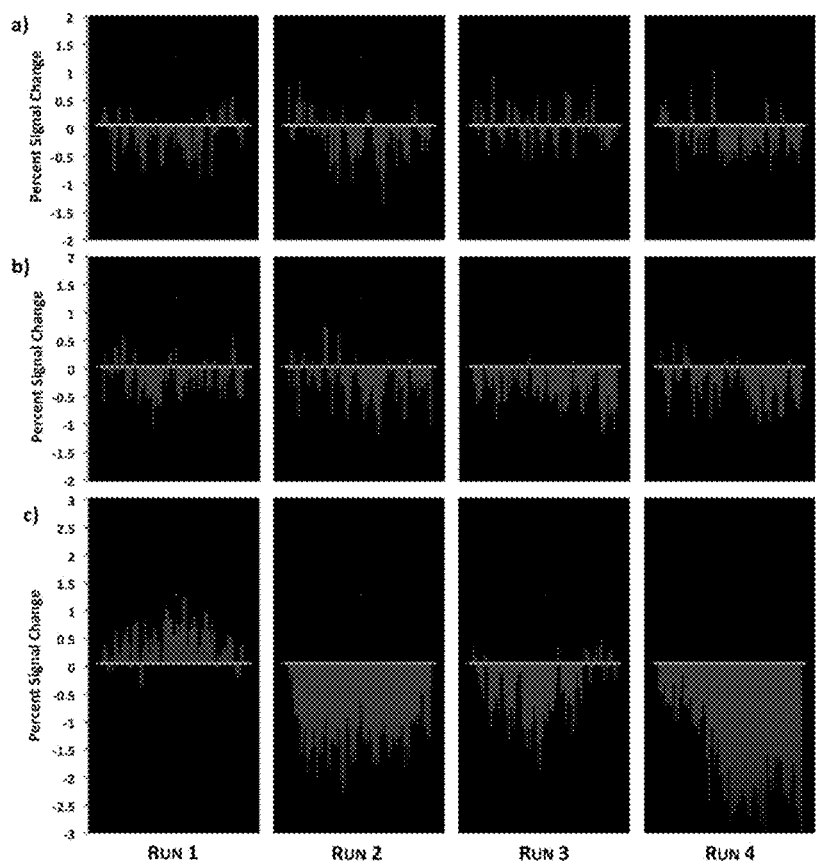
FIG. 5: Examples of rt-fMRI neurofeedback from meditators. Percent signal change (corrected for whole brain signal drift) from the PCC during feedback runs 1-4 are shown for a) subject #80, b) subject #93 and c) subject #43.
Figure 6:
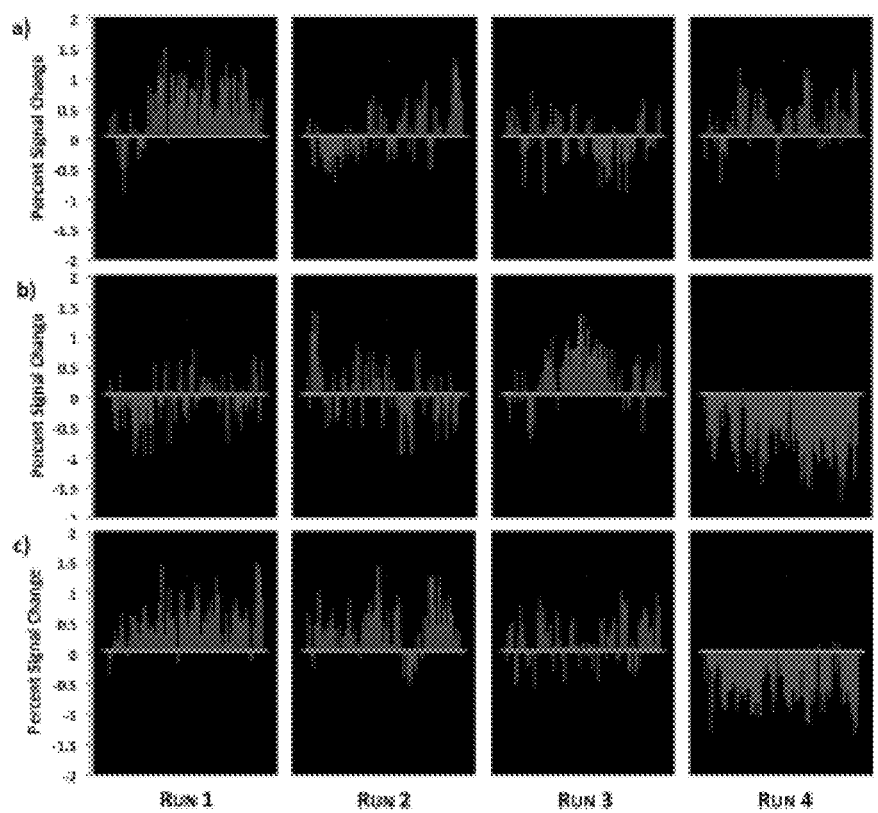
FIG. 6: Examples of rt-fMRI neurofeedback from controls. Percent signal change (corrected for whole brain signal drift) from the PCC during feedback runs 1-4 are shown for a) subject #70, b) subject #94 and c) subject #95.

In order to determine the relative sensitivity of rt-fMRI feedback from the PCC in correlation with subjective reports, individuals reported on their experience directly after each run and at the conclusion of their entire scanning session. Representative narratives from three meditators and three controls are shown below where we present the subject's reported correlation between self-experience and the displayed feedback and the subject's brief description of this correlation for feedback runs 1-4. If subjects were asked any additional questions or clarifications, the question present is preceded by a "Q:" and the subject's response is preceded by an "A:". The corresponding feedback presented to each subject is shown in FIG. 5 for the meditators and FIG. 6 for the controls. Finally, a fourth self-report with additional responses for runs 5 and 6 and the post-feedback interview from a meditator is presented in FIG. 7.

SUBJECT A (meditator, FIG. 5a). Run 1. Reported correlation: 7. How did I know? As I was getting used to looking at the image there was a lot of self-referential thoughts a lot of worries around it and as I was able to look away for a period of time and settle back into it. And the little red at the end, I don't know, I didn't feel so lost in thought at that period. Run 2. Reported correlation: 7. The red spots were me checking in with the graph. Yeah, the first one was definitely me checking in with the graph. The second one I don't know . . . . But the little ones were definitely. Run 3. Reported correlation: 6. The spike at the beginning was me thinking "I'm doing good look at all the blue I did" And after that I was starting to feel some discomfort in my feeling and thinking about how to alleviate it. And just getting into the patience of it and so there was a bit more red than I expected. Run 4. Reported correlation: 7. The smaller spikes again were me thinking about the pain in my finger. And the spikes at the end were me thinking "good job there is a lot of blue."

SUBJECT B (meditator, FIG. 5b). Run 1. Reported correlation: 8. Generally when . . . there were certain times when I registered thinking and the thoughts will come and those are the times that corresponded to the red spikes. Q: There are segments of deeper blue in the middle. Do you remember anything particular there? A: Yes, there was a slow inhale. I was very focused on the breath and it slowed down. Run 2. Reported correlation: 10. Well it seemed to be just at that same spot where the breath changes when you inhale and exhale. And it appears to roughly correspond with the red spikes. Q: And there were some deep blue in the middle. Did that correspond to anything particular? A: There are moments when the concentration is deep and the breath is very stable. Run 3. Reported correlation: 9. Well there were some thoughts. There were not many thoughts. There were some subtle thoughts that I thought would show up but didn't show up. Concentration was fairly smooth. Run 4. Reported correlation: 8. Same as before. I had a few more thoughts or concerns in the beginning, so that seems to be recorded in the more thinking. Q: And in the end I see some deeper blue. What was going on there? A: There was a kind of . . . it felt more stable, the breath and the focus.

SUBJECT C (meditator, FIG. 5c). Run 1. Reported correlation: 8. I was aware during [the run] that mind was having gaps and differently focusing and strayed from breath. There was a background of thinking. Run 2. Reported correlation: 9. I was aware of being with the object—the breath. Run 3. Reported correlation: 9. I was conscious of mind being focused on breath. A third of the way in I looked at the graph. In the middle-relaxation, presence. [Then] it veered away. The red at the end was when I looked at the graph. Run 4. Reported correlation: 10. There was a sense of flow, being with the breath-flow deepened in the middle.

SUBJECT D (control, FIG. 6a). Run 1. Reported correlation: 3. At the beginning I felt it was correlating well and although I was just breathing and focusing, I kept seeing red so maybe at the end I got anxious but before I got anxious it stopped correlating. I was thinking did I move or something . . . . I don't think so. Run 2. Reported correlation: 9. At the beginning I wasn't checking in. And then like every time when I go and check in with the graph it looks like it is going red with a delay but [when I] wasn't paying attention to the graph it looked blue so it looked like it was correlating with the graph. And towards the end I was thinking this is really [neat? garbled] and so I wasn't really paying attention to my breath and so it turned red. Run 3. Reported correlation: 9. At the beginning was left over from the words and then every time I check in with the graph, it keeps going red again . . . and when I don't pay attention to the graph and just concentrate on my breathing it drops back into blue and when I didn't check for a long time it stayed blue for a long time. And at the end it was me being really impressed with this. Run 4. Reported correlation: 6. I feel like I was focusing on the task, like on my breathing and at some parts I did get anxious. But um yeah I felt like I was focusing on my breathing a lot more than before. I kept looking up and it was red all the time.

SUBJECT E (control, FIG. 6b). Run 1. Reported correlation: 10. I felt like that I was able to focus on breathing, but occasionally I would have a flickering thought. And I think that what the red shows. Q: I see in the beginning there is a little more sustained blue, did you notice anything different between that and any of the later parts? A: Ah, I think that there was an eyelash that I was bothering my eye a little bit. And that created a lot of wondering thoughts for a second. Run 2. Reported correlation: 10. I think that I was more wondering thoughts, when I'm not doing it right. It kinda looks like that. Q: And I notice a big red spike in the beginning and a big blue spike in the middle, anything that you noticed that correlated with those? A: I think in the beginning I wasn't quite sure if I was supposed to start, and I saw the graph move, and I was like wow, and I tried a lot harder to focus on my breathing and watch that. Run 3. Reported correlation: 4. I felt like that I was on, really concentrating on my breathing, but it looks like on the graph that I had a lot of wondering thoughts. Run 4. Reported correlation: 8. I was able to focus on my breathing, the physical sensation, and not thinking of breathing. But I felt like that I had [two?] wandering thoughts. Q: I'm sorry, did you say that you weren't thinking of breathing? A: Yeah, I was focused more on the physical sensation instead of thinking in and out.

SUBJECT F (control, FIG. 6c). Run 1. Reported correlation: 5. Because I felt like that I was more focused on my breath than the graph says. Run 2. Reported correlation: 7. I think I now realize that I thought that I was more focused on my breath than I was at the last one, comparing my experience from the last one to this one. Q: And that blue right there, what did that correlate with? A: Being really focused on my breath, that's the most intensely. Run 3. Reported correlation: 10. It just looks like that it tracks exactly . . . . I had nothing in, like I experienced definite blank spaces, mind wandering. Run 4. Reported correlation: 10. The run looks like what I exactly experienced feeling. Q: And what's the difference between this run and the previous run? A: I felt a lot more relaxed this time. Q: Anything else? A: It felt like less of a struggle to prevent my mind from wandering.

Figure 7:
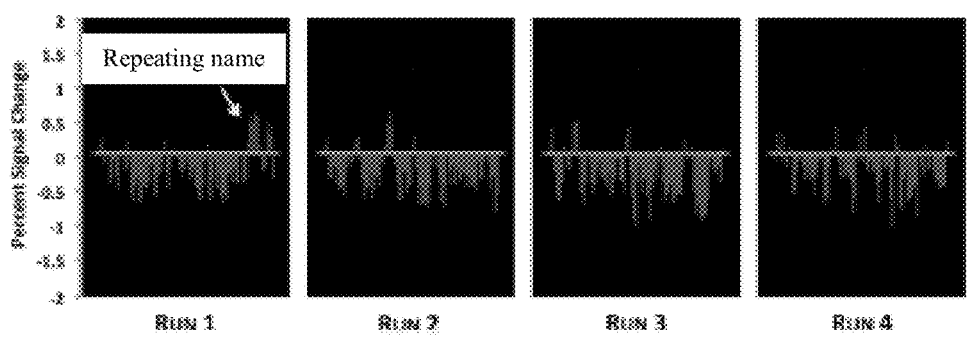
FIG. 7: Examples of rt-fMRI neurofeedback from meditator #37. Percent signal change (corrected for whole brain signal drift) from the PCC during feedback runs 1-6 are shown (run #5 shows feedback from posterior parietal cortex).

Subject G (meditator, FIG. 7). Run 1. Reported correlation: 8. I don't tend to have a lot of self reference. I tried to generate some at the end by saying my name over and over. Run 2. Reported correlation: 8. red peak in the middle—I had a memory of swimming in a pool Run 3. Reported correlation: 7. The second red spike at the beginning [I was] thinking about, evaluating the task. A couple of times in the middle [I was] thinking about reporting on what I was noticing Run 4. Reported correlation: 6. Little things. Run 5 (control region). Reported correlation: 6. I don't know what that big red part at the end was. Run 6. Reported correlation: 7. [At the] beginning, memory was red, second red was me discussing it with myself.

This individual also reported the following after finishing the rt-fMRI session. "Run 1 is interesting because after several minutes of blue, I wondered if this paradigm actually did measure self-referential processing so I effortfully broke the period of resting in awareness and generated a sense of self by saying "[my name], [my name], [my name]," while trying to visualize my face and sense of myself as a subject in the scanner "doing something". This produced a large red spike at the end of the run. OK . . . it works . . . interesting. Run 2 also shows an oscillation that I have noticed while meditating. There are certain "memory-images" that recurrently appear in practice, and there have been sets of them over the years. For example, for maybe 2 or 3 years, there was one memory-image of trees and vines that were on a path near my parents home that would appear recurrently in practice, especially at the beginning. In run 2, the memory-image is one of swimming at my aunt's swimming pool around age 8. This corresponds with the largest red spike in run 2. In Run 3+4, these two types of oscillations appear in the larger background of awareness. I also tried to focus more on breath sensations but quickly remembered how strained that felt because it created a subject object split of the watcher and breath. Between run 4 and run 6 (run 5 was the dummy), the real-time feedback was suggesting something that I had not considered: that these memory images, which I am not in (as an object), show up as red or self-referential. They don't have the same jarring tension or contracted feel to them as the other type of oscillation (when subject is separate from the object) so I have just assumed that nothing much is happening with them and kind of disregarded them as relevant. On Run 6, [Reported correlation: 7] I had a familiar memory image appear, one of a pond, willow tree and fields of my parents farm. I noticed the strong red deflection in response to this, although I don't appear in the image. I went back to the image to see if there was a sense of watcher-subject and noticed that image has a sense of being seen through a child's eyes. The somewhat desolate feeling landscape corresponds to that child's subjectivity. So there is a subject there, even though I never noticed it before, the scanner feedback made me look for it.

If you look at run 6 you can see me exploring the image in a long run of red in the middle. Then I remembered I wasn't doing the task so I let it go for a while. Then I started imagining myself in the future, telling Jud about what I had discovered about childhood memories, which you can see clearly in the second run of red at the end of run 6. I am sorry that I blew off the directions, but I learned something new and very subtle about those recurring memory-images that I have had for more than a decade. Something I may not have learned otherwise."

Example 3: Experienced Meditators More Easily Volitionally Decrease Activation in the PCC In experimental example 3, it was hypothesized that experienced meditators would be able to more easily volitionally decrease activation in the PCC compared to novice controls. Together, these results support the feasibility of using rt-fMRI feedback for linking first- and third-person data, and further establish the sensitivity and specificity of PCC activity for assessing mind-wandering and meditation.

The following methods were used in experimental example 3:

Using Rt-fMRI Neurofeedback as Feedback

Recent studies of meditation have suggested that the PCC is a key region of deactivation during meditation. As meditators and controls appeared to be learning key elements of meditation from their feedback sessions in Example 2 (relaxed focus, paying attention to the physical sensations of the breath rather than thinking about them etc.), and to confirm these literature reports, an additional task was administered to half of the subjects who completed Example 2. These individuals were instructed to decrease PCC activation as much as possible. Given meditator's previous experience at performing a meditation task in a selfless/non-'striving' way and the fact that novices may not be as adept, it was hypothesized that meditators would be able to more easily intentionally cause a relative decrease in PCC activation compared to controls. This is particularly important in that it has been hypothesized that the key to meditation is "not doing", suggesting the paradoxical notion that something is happening (attention is being paid, albeit to the sensation of the breath), without someone behind that action, which would theoretically increase PCC activation (Buddhaghosa, A. (1991), The path of purification: Visuddhimagga, Buddhist Publication Society; Goldstein, J. (1993), Insight meditation: the practice of freedom. Boston, Shambhala Publications; Gunaratana, H. (2002). Mindfulness in Plain English. Somerville, Mass., Wisdom Publications).

Subjects were the same as in Example 2 and were recruited sequentially throughout the second-half of that study (meditators, n=10; controls n=11). After completing the $6^{th}$ run of Example 2, and informing subjects whether run 5 or 6 was feedback from the control region, they were given the following instructions: "Now you have gotten a chance to see how activation of this region (the PCC) correlates with meditation. Given what you have learned from the previous runs, in the next run, please see how much you can actively make it go blue." Subjects then performed a single run and BOLD percent signal change in the PCC was calculated as described in Example 2.

Statistical Analysis of PCC Activation

Statistical analyses were performed on average BOLD percent signal change values using independent samples t-tests (SPSS/PASW 18 Inc; Chicago, Ill.). All tests of significance are two-tailed, and means are reported with ±standard deviation.

Figure 8:
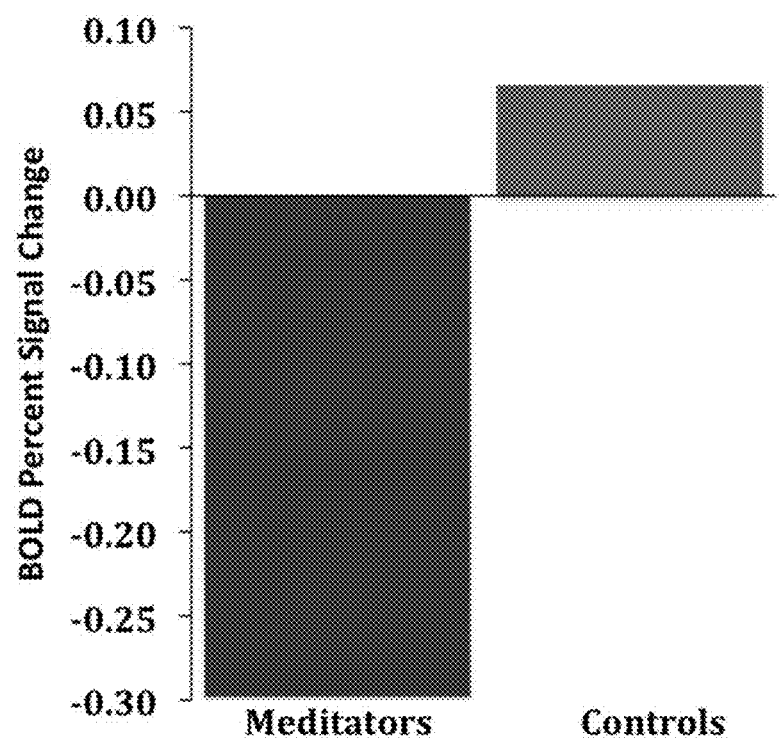
FIG. 8: Experienced meditators demonstrate relative PCC deactivation during meditation. Average percent signal change (corrected for whole brain signal drift) from the PCC during feedback run 7 is shown for meditators (blue) and controls (red). p=0.013.

As hypothesized, meditators demonstrated a significant voluntary reduction in PCC activation during meditation relative to controls (meditators=−0.30±0.32%; controls=0.07±0.29%; $t_{19}$=−2.73, p=0.013, FIG. 8).

Methods for improving the correlation between first-person reports of subjective experience and third-person measurement of neuronal activation have improved over the past few years, though clear hurdles remain. Rt-fMRI neurofeedback is a relatively new and promising technology that has demonstrated utility in a number of areas. However, it has not been tested for use in correlating first-person subjective experience with third-person objective observation. As demonstrated herein, using rt-fMRI neurofeedback for linking subjective reports to neuronal processes is feasible using the example of mind-wandering and meditative experience linked to PCC activation (Example 2). Not only did individuals report correlation between their mental state and the objective rt-fMRI data, but they also were able to discriminate between two highly temporally linked brain regions (the PCC and the posterior parietal cortex) in a significant manner, which provides validation to the accuracy and truthfulness of their reports (Example 2). Finally, meditators significantly voluntarily decreased activation in the PCC compared to controls, confirming previous reports of the PCC's role in meditative states (Example 3).

The data presented herein substantiates the proof-of-principal that using rt-fMRI neurofeedback in cognitive neuroscience studies is feasible. In studies designed to explore the correlation between self-reported experience of introspective brain states and their underlying neuro-mechanisms, such as presented herein, use of rt-fMRI with self-reports can achieve clear and reproducible results that are easily accessible to the subjects. Additionally, it obviates possible reverse inference of correlation between subject reports and objective data, as individuals report their direct experience as it correlates with neuronal activation without interference from a probe etc. It may also be useful in confirming or further teasing apart differential cognitive processes that may be hypothesized to activate certain brain regions. For example, Mason and colleagues linked mind-wandering to default mode network activation by training individuals 'to boredom' in a working memory task and measured average neuronal activity during blocks of a learned versus a novel working memory task (Mason, et al., 2007, Science 315(5810):393). As demonstrated herein, subjects reported their direct subjective experience of mind-wandering and its relative correlation with PCC activation, adding convergent validity and resolution to this theory that had not been demonstrated previously. However, it should be noted that this methodology, when used solely to document neural correlates of certain mind states (i.e., non-self-referential focus) is still limited to some degree by the interruption of the subject as observer, as highlighted by reports of the graph becoming red when individuals turned their attention to it.

Several questions that have been put forward in the literature about meditation can begin to be addressed. It sheds light on the question of whether default mode brain regions are involved in self-referential processes (i.e., is meditation truly 'selfless'?) by showing links between thinking about 'me' (self-referential focus) and increased activity in the PCC and, conversely, between a meditative (non-self-referential) focus and decreased activation of the PCC. Another question is, how does subjective relaxation affect meditation (and related PCC activity)? Indeed, subjective experiences both in novices and meditators from Example 2 give the first direct clues that a relaxed awareness of phenomena (e.g. the breath) is necessary for deactivation of regions involved in self-referential processing (e.g., the PCC), as has been previously hypothesized (Goldstein, J. (1993), Insight meditation: the practice of freedom. Boston, Shambhala Publications; Gunaratana, H. (2002), Mindfulness in Plain English. Somerville, Mass., Wisdom Publications; Taylor, et al., 2011, Neuroimage 57(4): 1524-1533). Example 3 indirectly supports this as well, as novices demonstrated an increase in PCC activation on average while 'trying' to make their graph go blue, while experienced meditators were significantly more effective at causing their graphs to be blue by 'allowing' themselves to drop into a meditative state. This may indicate the critical difference between 'someone' making something happen and 'dropping into' meditation, and/or "may reflect an adaptive process through which present-moment awareness is enhanced in individuals with long-term meditation experience, and information in the environment is processed with reduced distractibility and interference from self-referent thought or ruminative processes" (Taylor, et al., 2011, Neuroimage 57(4): 1524-1533).

As brain activity is notoriously 'noisy', rt-fMRI neurofeedback may be able to add a degree of sensitivity in linking subjective experience with neuronal activity that may otherwise be lost with block-design averaged regional activity. For example, Subject C (FIG. 5c) reported a deepening of the meditative state that correlated with significantly reduced PCC activation in run 4 vs. run 3. Additionally, Subject G reported nuanced experience that was linked to very minor changes in neuronal activity. Especially in individuals who may be trained to proficiency in particular tasks, such as meditation, these techniques may be remarkably suited for probing and refining first-person data (Lutz & Thompson, 2003, Journal of Consciousness Studies, 10(9-10): 31-52).

Real-time fMRI neurofeedback has been used in studies in which individuals empirically learned to train specific brain regions. These studies use trial-and-error to train subjects to literally gain control of their brains. This can be very time consuming, results are often variable and some individuals never acquire control (deCharms, 2008, Nat Rev Neurosci 9(9):720-729). As observed by Hampson, et al., individuals trained in this manner will often continue to try novel methods even after a successful method has been found (Hampson, et al., 2011, Brain Connectivity 1(1):91-98). This continued experimentation with different methods could confound these data sets. However, in instances in which cognitive techniques have been honed over many years (or centuries, in the case of meditation), this technology may be useful for confirming 'correct' techniques, especially those that are purely mental. With meditation, instruction can be maddeningly simple (e.g., "when sitting, just sit"), and thus conceptually difficult to convey. Surprisingly, several instances were found in which individuals spontaneously learned seemingly important distinctions between self-related processes, as indicated at first by increased PCC activation and later confirmed by their own subjective experience. For example, Subject E reported paying attention to the breath in run #3, but then noticed the difference between feeling the physical sensation of the breath as compared to thinking about it in the next run, which was highlighted by a complete reversal of PCC activation (FIG. 5b). Also, Subject F noticed that relaxation related to decreased PCC activation, while Subject G discovered a very subtle subjectivity related to an affective tone ("desolate feel . . . ") during meditation that s/he hadn't noticed before. These suggest that rt-fMRI neurofeedback may be used to augment traditional meditation instruction. As a yoga teacher provides feedback to guide one's posture, so too might a machine, one day, provide feedback on neuronal activation that correlates with 'striving', 'relaxation' and possibly even 'selfing'.

The data presented herein demonstrates the feasibility of using rt-fMRI neurofeedback for more tightly linking $1^{st}$ person subjective experience with $3^{rd}$ person objective measurement without interrupting the on-going experience. These results also demonstrate that this type of feedback can be sensitive and relatively specific, given a particular task(s) and brain region. Finally, this data also suggest the possibility of using rt-fMRI neurofeedback for the augmentation and/or calibration of specific mental training techniques such as meditation.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of correlating a subject's at least one subjective report to at least one neuronal process of the subject, the method comprising:
   measuring a subject's PCC activity by fMRI;
   presenting a representation of said subject's PCC activity to the subject simultaneously with said measuring;
   subsequently instructing the subject to provide a report of the subject's mental state at the time of said presenting the representation of the subject's PCC activity to the subject; and
   subsequently creating a correlation by
      re-presenting said representation to said subject wherein said subject identifies features in the representation during said re-presenting: and
      recording a subjective report from said subject of a mental state of the subject at the time of a brain region activity measurement wherein said subjective report includes a correlation report from the subject of their subjective experiences and the representation, the subject's responses about the features identified by said subject and said features' relationship to the mental state of the subject.

2. The method of claim 1, wherein the representation of the subject's PCC activity is presented to the subject via one or more selected from the group consisting of: a visual display, an interactive visual display, an auditory signal, and a tactile signal.

3. The method of claim 1, further comprising:
   measuring at least one additional brain activity in the subject's brain selected from the group consisting of the following brain regions: dorsal anterior cingulate, dorsolateral prefrontal cortex, posterior parietal cortex, posterior insula, and thalamus;
   presenting a representation of the subject's at least one additional brain activity to the subject simultaneously with said measuring at least one additional brain activity; and subsequently instructing the subject to provide a report of the subject's mental state at the time of said presenting the representation of the subject's at least one additional brain activity.

4. A method of correlating a subject's at least one subjective report to at least one neuronal process of the subject, the method comprising:

measuring activity of at least one specific brain region of a subject's brain with a brain activity imaging device;

presenting a representation of said activity of said at least one specific brain region via at least one sensory mechanism to the subject simultaneously with said measuring;

subsequently creating a correlation by re-presenting said representation to said subject wherein said subject identifies features in the representation during said re-presenting; and recording a subjective report from said subject of a mental state of the subject at the time of said brain region activity measurement, wherein said subjective report includes a correlation report from the subject of their subjective experiences and the representation, the subject's responses about the features identified by said subject, and said features' relationship to the mental state of the subject.

5. The method of claim 4, wherein said brain activity imaging device is selected from the group consisting of: fMRI and EEG.

6. The method of claim 4, wherein said brain activity imaging device is an fMRI.

7. The method of claim 4, wherein said brain activity imaging device is an EEG.

8. The method of claim 4, wherein said at least one sensory mechanism is selected from the group consisting of: a visual display, an interactive visual display, an auditory signal, and a tactile signal.

9. The method of claim 4, further comprising:

measuring activity of at least one additional specific brain region in said subject's brain;

presenting a representation of said at least one additional specific brain region activity via the at least one sensory mechanism to the subject simultaneously with said measuring activity of said at least one additional specific brain region;

subsequently collecting a subjective report from said subject of the subject's mental state at the time of said presented representation of said at least one additional specific brain region activity; and correlating said subjective report from said subject of the subject's mental state at the time of said presented representation of said at least one additional brain region activity with said at least one additional specific brain region activity measurement.

10. The method of claim 4, wherein said at least one specific brain region is selected from the group consisting of: PCC, dorsal anterior cingulate, dorsolateral prefrontal cortex, posterior parietal cortex, posterior insula, and thalamus.

11. The method of claim 4, wherein said at least one specific brain region is a PCC.

* * * * *